US012410429B2

(12) United States Patent
Peters

(10) Patent No.: US 12,410,429 B2
(45) Date of Patent: Sep. 9, 2025

(54) COMPOSITIONS AND METHODS FOR GENE TARGETING USING CRISPR-Cas AND TRANSPOSONS

(71) Applicant: Cornell University, Ithaca, NY (US)

(72) Inventor: Joseph E. Peters, Ithaca, NY (US)

(73) Assignee: Cornell University, Ithaca, NY (US)

( * ) Notice: Subject to any disclaimer, the term of this patent is extended or adjusted under 35 U.S.C. 154(b) by 953 days.

(21) Appl. No.: 17/438,427

(22) PCT Filed: Mar. 16, 2020

(86) PCT No.: PCT/US2020/022964
§ 371 (c)(1),
(2) Date: Sep. 11, 2021

(87) PCT Pub. No.: WO2020/186262
PCT Pub. Date: Sep. 17, 2020

(65) Prior Publication Data
US 2022/0145298 A1    May 12, 2022

Related U.S. Application Data

(60) Provisional application No. 62/882,204, filed on Aug. 2, 2019, provisional application No. 62/818,523, filed on Mar. 14, 2019.

(51) Int. Cl.
*C12N 15/113* (2010.01)
*C07K 14/195* (2006.01)
*C12N 9/12* (2006.01)
*C12N 15/10* (2006.01)
*C12N 15/11* (2006.01)
*C12N 15/63* (2006.01)
*C12N 15/90* (2006.01)

(52) U.S. Cl.
CPC .......... *C12N 15/113* (2013.01); *C12N 9/1241* (2013.01); *C12N 15/102* (2013.01); *C12N 15/111* (2013.01); *C12N 15/63* (2013.01); *C12N 15/90* (2013.01); *C12N 2310/20* (2017.05); *C12N 2800/90* (2013.01)

(58) Field of Classification Search
CPC .............................. C12N 15/90; C12N 15/113
See application file for complete search history.

(56) References Cited

U.S. PATENT DOCUMENTS

| | | | |
|---|---|---|---|
| 6,017,730 | A | 1/2000 | Molin et al. |
| 7,893,251 | B2 | 2/2011 | Lorenz |
| 10,041,051 | B2 | 8/2018 | Hsieh et al. |
| 2010/0222410 | A1 | 9/2010 | Davies et al. |
| 2019/0000896 | A1 | 1/2019 | Lichtenstein et al. |
| 2020/0002746 | A1 | 1/2020 | Mellor et al. |

OTHER PUBLICATIONS

A0A2T4N0S0_AERVE; https://www.uniprot.org/uniprotkb/A0A2T4N0S0/entry (Published Jul. 18, 2018) (Year: 2018).*
Chen, F., Ding, X., Feng, Y. et al. Targeted activation of diverse CRISPR-Cas systems for mammalian genome editing via proximal CRISPR targeting. Nat Commun 8, 14958 (2017), pp. 1-12. https://doi.org/10.1038/ncomms14958 (Year: 2017).*
Zetsche B, Gootenberg JS, Abudayyeh OO, Slaymaker IM, Makarova KS, Essletzbichler P, Volz SE, Joung J, van der Oost J, Regev A, Koonin EV, Zhang F. Cpf1 is a single RNA-guided endonuclease of a class 2 CRISPR-Cas system. Cell. Oct. 22, 2015;163(3):759-71. doi: 10.1016/j.cell.2015.09.038. (Year: 2015).*
Zheng, Yanli, et al. "Characterization and repurposing of the endogenous type I-F CRISPR-cas system of Zymomonas Mobilis for genome engineering." Nucleic Acids Research, vol. 47, No. 21, Oct. 24, 2019, pp. 11461-11475, https://doi.org/10.1093/nar/gkz940. (Year: 2019).*
Peters, J.E., et al., Recruitment of CRISPR-cas systems by Tn7-like transposons, Proc Natl Acad Sci USA, Aug. 15, 2017, vol. 14, No. 35, pp. E7358-E7366.
Genbank AMQ42792.1, hypothetical protein AMS64_10640 [Aeromonas veronii], NCBI, Mar. 16, 2016, 2 pages. https://www.ncbi.nlm.nih.gov/protein/AMQ42792.1/.
Genbank CP022176.1, Aeromonas salmonicida strain S44 plasmid pS44-1, complete sequence, Jul. 3, 2017, pages. https://www.ncbi.nlm.nih.gov/nuccore/CP022176.1/.
Genbank CP012504.1, Aeromonas veronii strain TH0426, complete genome, Mar. 16, 2016, 5 pages. https://www.ncbi.nlm.nih.gov/nuccore/CP012504.1.
Parks, A.R., Tn7 Transposes into Replicating DNA Using an Interaction with the Processivity Factor, Facilitating Genome Evolution, Thesis, Cornell University, Aug. 2008, 225 pages.
McDonald, N.D., et al., CRISPR-Cas systems are present predominantly on mobile genetic elements in *Vibrio* species, BMC Genomics, Feb. 4, 2019, vol. 20, No. 105, pp. 1-23.
NCBI Reference Sequence WP_113995226.1, endonuclease [Aeromonas hydrophila], Jul. 18, 2018, 1 page.
NCBI Reference Sequence WP_064336210.1, hypothetical protein [Aeromonas veronii], May 28, 2016, 1 page.
NCBI Reference Sequence WP_107683714.1, endonuclease [Aeromonas veronii], Apr. 18, 2018, 1 page.
NCBI Reference Sequence WP_125601551.1, endonuclease [Aeromonas salmonicida], Dec. 19, 2018, 1 page.
Genbank AXV19226.1, endonuclease [Aeromonas veronii], NCBI, Sep. 7, 2018, 2 pages.

* cited by examiner

*Primary Examiner* — Jennifer Dunston
*Assistant Examiner* — Alexandra Rose Lippolis
(74) *Attorney, Agent, or Firm* — Hodgson Russ LLP

(57) ABSTRACT

Provided are compositions and methods for transposon-CRISPR-based DNA editing. The compositions and methods include a modified TnsA protein that is altered from its original sequence found in *Aeromonas salmonicida*, and provides improved transposition frequency, and is functional in a heterologous system. The TnsA protein is used in a system with transposon proteins TnsB, TnsC, TniQ, Cas proteins Cas8f, Cas5f, Cas7f, Cas6f, a transposable DNA cargo sequence that is flanked by left and right transposon sequences, and at least one guide RNA that contains at least one spacer targeted to a target DNA sequence in the chromosome or the extrachromosomal element.

14 Claims, 18 Drawing Sheets
Specification includes a Sequence Listing.

COMPOSITIONS AND METHODS FOR GENE TARGETING USING CRISPR-Cas AND TRANSPOSONS

CROSS REFERENCE TO RELATED APPLICATIONS

This application claims priority to U.S. provisional patent application No. 62/818,523, filed Mar. 14, 2019, and U.S. provisional patent application No. 62/882,204, filed Aug. 2, 2019, the entire disclosures of each of which are incorporated herein by reference.

FIELD

The present disclosure relates generally to approaches for targeting genes and more particularly for improved compositions and methods using combinations of Tn7-like transposons with Cas8/5f, Cas7f, and Cas6f for improved and flexible chromosome editing.

BACKGROUND

Existing CRISPR-Cas systems can similarly be used to deliver DNA to a specific site in a single orientation. However, these processes involve a cumbersome two-step process where the CRISPR-Cas system and guide RNA are first used to break the host chromosome. In a second process, a DNA substrate that must be introduced at the same time must then be used by another form of DNA recombination to repair the DNA break by replacing it with an investigator introduced DNA substrate. This recombination process is often a natural host recombination system but sometimes another synthetic system expressed in the host. This is an inefficient process that can also lead to unwanted off-target events. There is accordingly on ongoing and unmet need for improved CRISPR-based approaches to chromosome editing. The present disclosure is pertinent to this need.

SUMMARY OF THE DISCLOSURE

The present disclosure provides compositions and methods for modifying chromosomes and extra-chromosomal elements, the latter including but not necessarily limited to plasmids, viral or other pathogen-derived DNA, and DNA present in, for example, organelles in eukaryotic cells, such as mitochondria and chloroplasts. DNA modified according to the present disclosure may be cytoplasmic or nuclear DNA, and acts on double stranded DNA. The disclosure includes modification of double-stranded DNA templates without inducing double-stranded breaks, and thus in embodiments comprises transposing a segment of a double stranded DNA to another location, in cis or in trans.

The disclosure is illustrated in non-limiting embodiments by demonstrating transposition from a prokaryotic chromosome to a plasmid, and transposition from one location in a prokaryotic chromosome to another location in the same chromosome. It is accordingly considered that the system is readily adaptable for use in eukaryotic cells and organisms, using the same set of proteins and/or vectors encoding the proteins, by configuring the proteins as needed to be located in the nucleus of eukaryotic cells.

The disclosure, at least in part, provides for increased transposition efficiency, relative to suitable controls, as described further below. In embodiments, the disclosure includes use of a modified TnsA protein for which an unmodified counterpart was initially identified as encoded by *Aeromonas salmonicida* strain S44, on its plasmid pS44-1. By analysis that is described more fully below, and without intending to be bound by any particular theory, it is considered that the wild type TnsA protein encoded by the pS44-1 plasmid is non-functional in its native environment. The disclosure accordingly includes a modified version of this protein that is functional in the presently described system, and moreover is functional in at least one heterologous system, illustrated in non-limiting embodiments using *E. coli*. Thus, the disclosure provides, in one embodiment, a method for modifying a chromosome or extrachromosomal element in one or more heterologous cells.

A method of the disclosure generally comprises introducing into one or more cells a TnsA transposon protein that is at least 90% similar to SEQ ID NO:1 but contains an amino acid other than Alanine at position 125 of SEQ ID NO:1, or by introducing into the cells an expression vector comprising a tnsA gene that encodes and expresses the modified TnsA transposon protein when introduced into one or more cells. The modified TnsA protein functions in the context of transposon proteins TnsB, TnsC, TniQ, and Cas proteins Cas8f, Cas5f, Cas7f, Cas6f, examples of which are known in the art and are adaptable for use with the presently provided system. The method also comprises a transposable DNA cargo sequence that is flanked by left and right transposon sequences, said left and right transposon sequences being readily recognizable by those skilled in the art, and at least one guide RNA comprising a spacer targeted to a target DNA sequence in the chromosome or the extrachromosomal element. The DNA target sequence comprises a protospacer and a protospacer adjacent motif (PAM) that is 5' to the protospacer. Thus, the spacer in the guide RNA may be complementary to a protospacer. By providing cells that comprise each of these components, the disclosure facilitates the guide-RNA directed transposition of any desired DNA cargo into the chromosome or extrachromosomal element in a location selected by the user of this system. The location of the transposition is generally 3' relative to the PAM and the protospacer sequence, following established principles of Tn7 transposition events with respect to nucleotide positions that are known in the art.

In certain implementations, the TnsA transposon protein is at least 90% similar to SEQ ID NO:1 and comprises an amino acid that is not Alanine at position 125 of SEQ ID NO:1. In a non-limiting embodiment, the TnsA transposon protein comprises a D at position 125 of SEQ ID NO:1, or a sequence that is at least 90% identical to SEQ ID NO:1, with the proviso that position 125 is not Alanine. In embodiments, the TnsA protein comprises SEQ ID NO:2, which includes a A125D change, relative to the amino acid sequence of SEQ ID NO:1.

In embodiments, a chromosome or extrachromosomal element that is modified according to the present disclosure is present in one or more prokaryotic cells. In embodiments, a chromosome or extrachromosomal element that is modified according to the present disclosure is present in one or more eukaryotic cells. In embodiments, efficiency of transposition of the transposable DNA cargo in a population of cells is more efficient than transposition obtained from a control value. In embodiments, the control value is obtained using a TnsA transposon protein that comprises an amino acid sequence that is at least 90% similar to SEQ ID NO:1 and contains an Alanine at position 125.

The disclosure includes introducing the described proteins, DNA encoding the proteins, and ribonucleoprotein complexes, directly into cells. In embodiments, the disclosure thus includes introducing into cells one or more expression vectors that encode at least one of the TnsA, TnsB, TnsC, TniQ, Cas8f, Cas5f, Cas7f, and Cas6f proteins. The disclosure also includes modifying DNA in cells that endogenously express one or more of these proteins, provided at least one of the proteins is introduced into the cells. Likewise, the DNA cargo to be transposed in a guide-RNA directed manner may be provided as one or more distinct molecules, or may be present on one or more of the expression vectors, or by a distinct vector, or may be pre-existing in the cell or cells to be modified, i.e., the disclosure includes transposition of an endogenous DNA element. In non-limiting embodiments, the transposable DNA cargo sequence is transposed into the chromosome or extrachromosomal element within 42-52 nucleotides 3' relative to the 3' end of the protospacer. In embodiments, the transposable DNA cargo is inserted in an orientation with the right end proximal to the protospacer. In embodiments, this orientation occurs in all insertions in a population of cells.

Expression vectors encoding one or more proteins described herein are included in the disclosure, as are cells that comprise such expression vectors. The disclosure includes such expression vectors in combination with a transposable DNA cargo sequence that is flanked by left and right transposon sequences. Cells modified using the compositions and methods of the disclosure are also included.

Also provided are kits for use in a method of this disclosure. The kit includes an expression vector encoding a TnsA transposon protein that is at least 90% similar to SEQ ID NO:1 but contains an amino acid other than Alanine at position 125 of SEQ ID NO:1. The kit may also include one or more expression vectors that encode one or a combination of TnsB, TnsC, TniQ, Cas8f, Cas5f, Cas7f, and cas6f. The kit may also include an expression vector configured for accepting a sequence encoding a suitable guide RNA to facilitate RNA-guided transposition of any desired DNA cargo to any desired location.

BRIEF DESCRIPTION OF THE DRAWINGS

FIG. 2—Panel A—Transposon and Cas proteins are expressed in bacteria or other cell type where the DNA insertion is desired. A guide RNA is designed such that it matches the position of interest in the cell. FIG. 2 Panel B. Illustration of expression of the guide RNA and the DNA to be delivered are shown in a non-limiting embodiment on a separate plasmid. DNA oligonucleotides encoding the guide RNA are shown as cloned into a synthetic CRISPR array on the plasmid. The desired genes or other DNA cargo to be delivered into this site are cloned into the vector using standard molecular techniques using a multicloning (MCS) site located between the left and right end transposon sequences in the vector. The delivery vector facilitates expression of the guide RNA in the target host cell(s). In one variation of this procedure, such as in prokaryotes, the plasmid will not be maintained, but will allow the genes of interest or other DNA to be delivered to the target site recognized by the guide RNA. For ease of selecting the desired insertion, a drug resistance marker can also be included in the vector (DrugR).

DETAILED DESCRIPTION

Figure 1:
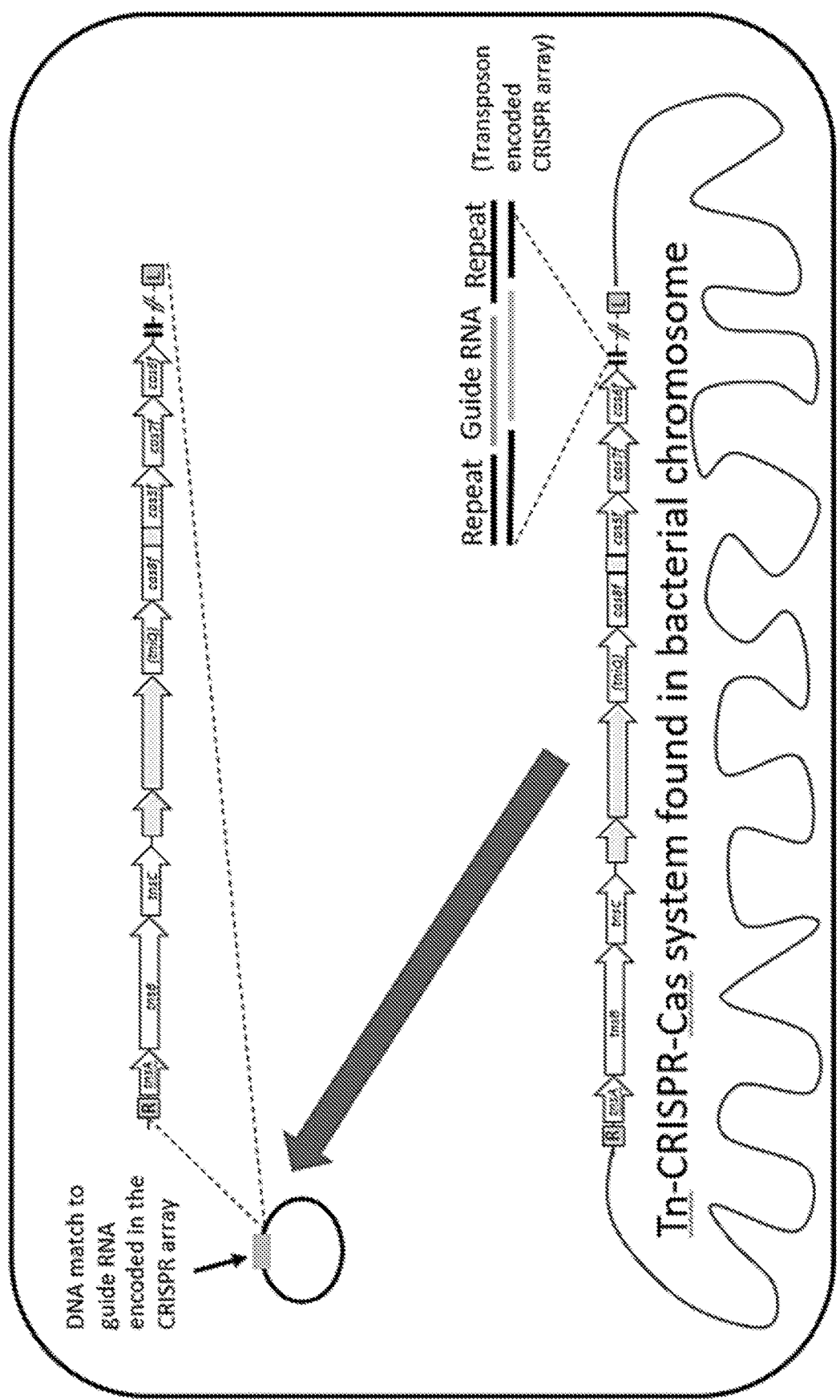
FIG. 1. Cartoon depiction illustrating Tn7-like CRISPR-Cas system targeting transposon insertions adjacent to matches to the guide RNA. The Guide RNA is encoded between repeats in the CRISPR array on the element. Insertions occur in one orientation based on the Left (L) and Right (R) end-sequences of the transposon.

Unless defined otherwise herein, all technical and scientific terms used in this disclosure have the same meaning as commonly understood by one of ordinary skill in the art to which this disclosure pertains.

Every numerical range given throughout this specification includes its upper and lower values, as well as every narrower numerical range that falls within it, as if such narrower numerical ranges were all expressly written herein.

The disclosure includes all polynucleotide and amino acid sequences described herein. Each RNA sequence includes its DNA equivalent, and each DNA sequence includes its RNA equivalent. Complementary and anti-parallel polynucleotide sequences are included.

Every DNA and RNA sequence encoding polypeptides disclosed herein is encompassed by this disclosure. Amino acids of all protein sequences and all polynucleotide sequences encoding them are also included, including but not limited to sequences included by way of sequence alignments. Sequences of from 80.00%-99.99% identical to any sequence (amino acids and nucleotide sequences) of this disclosure are included.

The disclosure includes all polynucleotide and all amino acid sequences that are identified herein by way of a database entry. Such sequences are incorporated herein as they exist in the database on the filing date of this application or patent.

The disclosure includes polynucleotides encoding proteins of this disclosure, and polynucleotides that comprise transposons, including but not necessarily limited to Tn7- like transposons. In certain approaches of this disclosure expression vectors, such as plasmids, are used to produce one or more than one construct and/or component of the system, and any of their cloning steps or intermediates. A variety of suitable expression vectors known in the art can be adapted to produce components of this disclosure.

In embodiments, the disclosure provides adaptations of type I-F CRISPR-Cas systems. In embodiments, the disclosure provides adaptations of Type I-B CRISPR-Cas systems. In embodiments, the disclosure provides adaptations of Tn7-like transposons. In particular, bacterial genomes shows that many Tn7-like transposons contain 'minimal' type I-F CRISPR-Cas systems that contain of fused cas8f and cas5f, cas7f and cas6f genes, and a short CRISPR array. Additionally, several small groups of Tn7-like transposons encompass similarly truncated type I-B CRISPR-Cas systems. This gene composition of the transposon-associated CRISPR-Cas systems implies that they are competent for pre-crRNA processing yielding mature crRNAs and target binding but not target cleavage that is required for interference. Accordingly, in developing aspects of the present disclosure, e.g., to identify elements that could potentially be adapted for use in the presently described approaches, approximately 400 elements were initially analyzed by searching for elements that are highly represented with uninterrupted genes and contiguous right and left transposon end sequences where closely related transposons were found in separate species. These elements from hosts in the family Vibrionaceae, were assembled in expression systems that are regulatable in *E. coli*, and were tested for guide RNA-directed transposition activity. This approach did not provide any reliable evidence that transposition activity had occurred. A significant amount of additional analysis and experiments were carried out by altering expression construct promoters, translation signals, and general operon structure, and to establish genetic systems where low levels of transposition could be detected, but where background was also low to minimize false positives. This approach also did not identify evidence of guide RNA-directed transposition activity using these systems in heterologous hosts. The possibility that host factors endogenous to the original host were required was then analyzed. In particular, experiments were carried out to integrate promoters into the native host to drive expression of the operons to determine evidence of transposition. These experiments also gave no evidence of detectable transposition. It was accordingly unclear if the analyzed elements were inactivated by, for example, unknown missense mutations, or only active during a special cycle of growth, or in the presence of a special inducing factor, or naturally transposed at a frequency lower than the detection limit of the system. In response to these failed attempts to identify components that could be used in the presently described system, a more advanced method was employed. Specifically, attempts were made to identify candidate Tn7-CRISPR/Cas elements with the type I-F variant systems from a larger pool of sequences. This approach was taken in part to identify potential candidate elements that could be deliberately modified so that they would be suitable for genome editing by guide RNA-directed transposition, particularly in heterologous hosts. To this end, we analyzed approximately 300,000 genomes, and in turn focused on the gammaproteobacterial class of bacteria. This latter approach included analysis of approximately 45,000 genomes from distinct bacterial types, one non-limiting example of which included all transposon proteins from *Aeromonas hydrophila*, including but not limited to its TnsA protein. Specifically, we analyzed the sequence of gammaproteobacterial genomes for the signature proteins of TnsA, TnsB, TnsC, TniQ/TnsD, Cas8/5f, Cas7f, and Cas6f using the definitions in the pfam database (pfam.xfam.org/). The gene location information was used to computationally determine the convergence of these genes with the expected operon structure. This lead to a collection of just under 800 candidate Tn7-CRISPR/Cas elements with the I-F variant systems. The majority of elements were found to reside in species from within the bacterial family Vibrionaceae within the gammaproteobacteria, which, without intending to be bound by any particular theory is to be considered to be where they likely originated. Based in part on this analysis, we focused on elements found outside the Vibrionaceae in view of our hypothesis that they may have accumulated alleles that made them less dependent on host factors. We therefore attempted to identify and refine a system that was not found in a Vibrionaceae.

A computationally-assisted decision matrix was developed that took into account criteria including location where the bacterial host was originally isolated, phylogenetic relatedness of the bacterial hosts, and amino acid variability weighed by the domain structure and active sites within the seven Tns/Tni/Cas proteins. We also took into account that alleles with increased activity often come with host fitness costs, selecting for secondary and confounding moderating alleles. This analysis identified the genus *Aeromonas* as a potential source of elements that could be modified for use in the presently described system. We produced a number of candidate alleles which could be tested for the capability to cause guide RNA-directed transposition in a heterologous system, using as a non-limiting demonstration the non-native *E. coli* host. Based at least in part on this analysis, the pool of alleles was used to identify a number of potential amino acid changes in *Aeromonas* proteins that could potentially convert a system that does not exhibit desired guide RNA-directed transposition functionality in its native host, let alone in a heterologous host, into a system that exhibits desired guide RNA-directed transposition functionality in a heterologous host. Accordingly, the present disclosure provides, in one embodiment, a modification of the TnsA protein that is encoded by *Aeromonas salmonicida* strain S44 plasmid pS44-1. In this regard, the present disclosure shows using representative assays that a single amino acid change in this TnsA protein is necessary and sufficient to convert the presently described system from a non-functional to a functional guide RNA-directed transposition system in a heterologous host. Specifically, a change in the TnsA protein of residue 125 from Alanine (A) to Aspartic Acid (D) was able to impart guide RNA-directed transposition functionality in the representative heterologous system of *E. coli*. This novel functionality was not expected based the genomic context of TnsA in its closest relative (*Aeromonas hydrophila*) which has the same or similar sequences and is unambiguously non-functional, in the native host. The system thus, in part, may exploit of Tn7-like transposons that naturally control target site selection, but comprise certain DNA and amino acid changes that are further described herein.

In embodiments, the compositions and methods of this disclosure are functional in a heterologous system. "Heterologous" as used herein means a system, e.g., a cell type, in which one or more of the components of the system are not produced without modification of the cells/system. A non-limiting embodiment of a heterologous system is any bacteria that is not *Aeromonas salmonicida*, including but not necessarily limited to *Aeromonas salmonicida* strain S44. In embodiments, a representative and non-limiting heterologous system is any type of *E. coli*. A heterologous system also includes any eukaryotic cell.

In embodiments, any protein of this disclosure may be an *Aeromonas salmonicida* strain S44 protein, or a derivative thereof, with the exception that the TnsA protein is not produced by *Aeromonas salmonicida* strain S44, without modification, such as by recombinant engineering of the type described further herein.

In embodiments, the presently described systems are used to direct blocks of genes to virtually any position in a bacterial genome, any episomal element, or a eukaryotic chromosome, in an orientation dependent fashion. In embodiments, the system is thus targeted to a sequence in a chromosome in a eukaryotic cell, or to a DNA extrachromosomal element in a eukaryotic cell, such as a DNA viral genome. Thus, the disclosure includes modifying eukaryotic chromosomes, and eukaryotic extrachromosomal elements. Accordingly, the type of extrachromosomal elements that can be modified according to the presently described compositions and methods are not particularly limited.

As known in the art, transposons are genetic elements that can move within a genome that appear to be found in all forms of life. As discussed above, the present disclosure relates in part to a version of the Tn7-like element where it has adapted the CRISPR-Cas system as a mechanism of targeting where the transposon moves, and further comprises mutations in certain Tn-related proteins that enhance CRISPR-Cas based editing using transposon proteins.

CRISPR-Cas systems are typically naturally found as acquired immune systems in bacteria. They utilize short genetic features known as "guide RNAs" as a mechanism to destroy DNAs that invade the cell. The guide RNAs are encoded in what is known as a CRISPR array that is processed with CRISPR associated proteins (or Cas proteins) to make a complex (Cas proteins+guide RNA) to target DNAs that match the guide RNA sequence for destruction by cleaving the DNA. The naturally occurring element has evolved to use a subset of the Cas proteins (Cas8/5f, Cas7f, and Cas6f) to process a cognate CRISPR array containing the guide RNA to target a cognate Tn7-like element to direct transposition adjacent to the DNA match to the guide RNA sequence. As is known in the art, Cas8/5f (also referred to as Cas8-5) are naturally fused in I-F variant systems associated with Tn7-like elements. The transposon proteins involved in this process are TnsA, TnsB, TnsC, and TnsD/TniQ. They recognize cognate "left" and "right" transposon DNA sequences that flank the transposon. Thus, as is also known in the art, each left and right end sequence pair is ordinarily associated with a particular set of tnsA, tnsB and tnsC genes, and the left and right end sequences are considered "cognate" with respect to the particular tnsA, tnsB and tnsC cassette. In addition to the I-F systems that are modified as described herein, the disclosure includes adapting other systems, including but not necessarily limited to type I-B CRISPR/Cas systems.

The present disclosure demonstrates that transposon and CRISPR-Cas systems can be used in cells to target insertion of the element into a single position adjacent to the match to the guide RNA in one orientation (see, for example, FIG. 1). This system has been recapitulated using recombinant approaches such that the transposon proteins and Cas proteins can be expressed in any position in the cell and they will act on the CRISPR array and transposon end-sequences found elsewhere in the cell.

Figure 2:
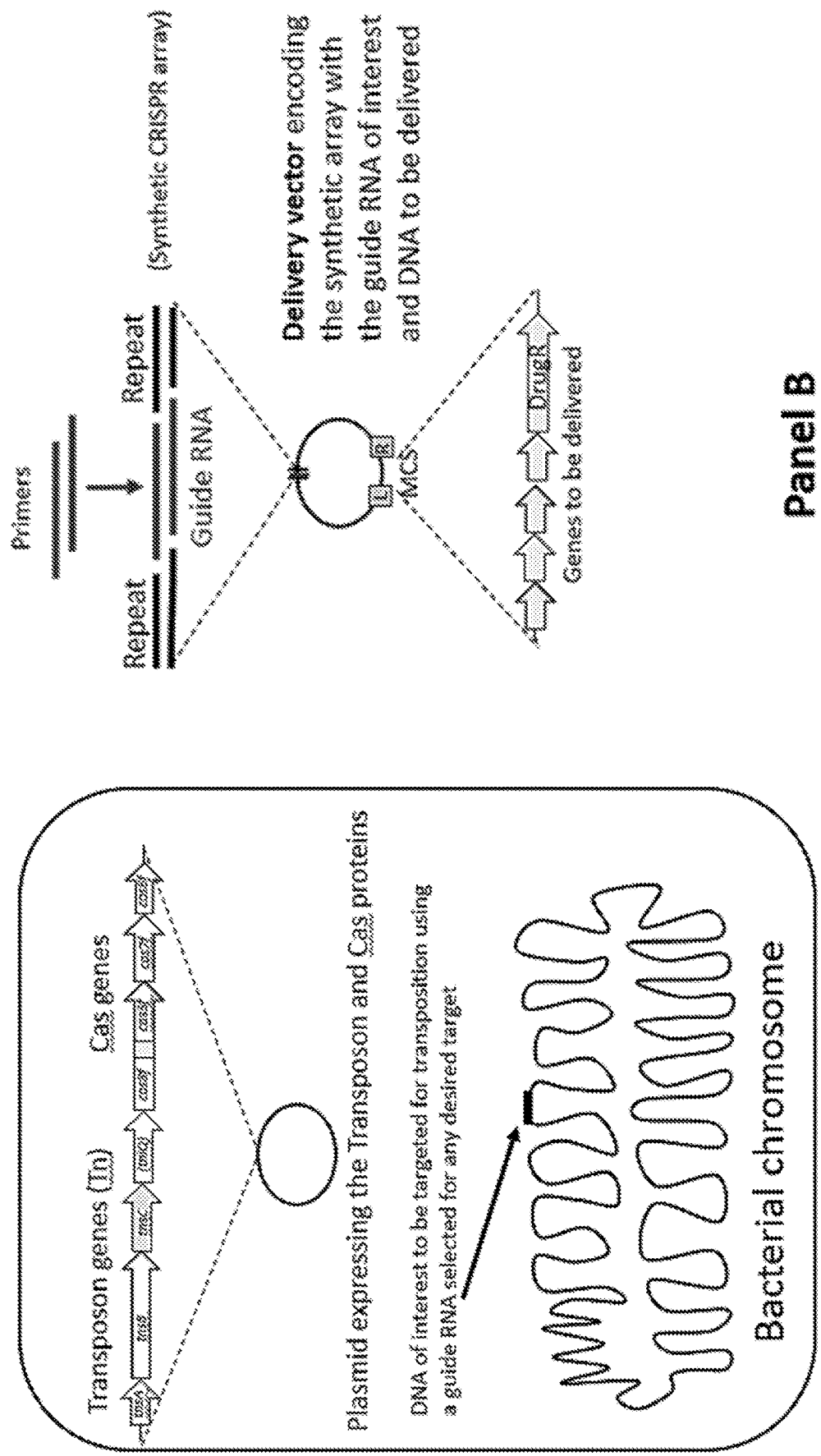
FIG. 2. Illustration of a representative embodiment of the disclosure. In the illustrated system, the transposon (Tn) and Cas proteins as described herein are expressed, for example, from a plasmid. These proteins catalyze the movement of the genes of interest, such as DNA cargo, into a selected target in the bacterial genome, or on a plasmid.
Figure 3:
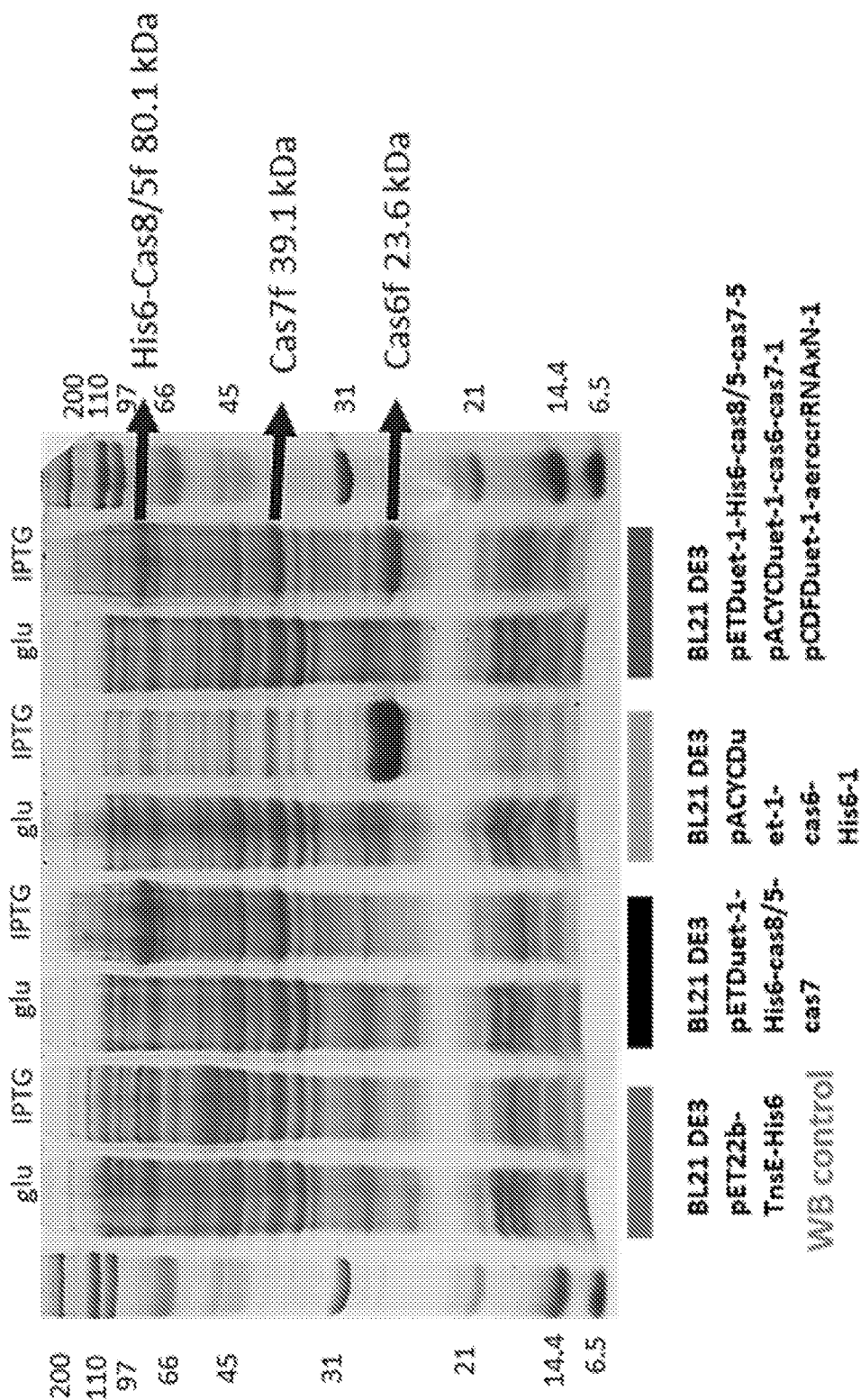
FIG. 3. Representative photograph of electrophoretic separation and sizes of Cascade proteins produced recombinantly. In non-limiting embodiments, proteins derived from, for example, *Aeromonas* strains, can be produced in *E. coli* using different promoters from separate vectors, in individual cells or jointly in the same strain background. Markers designate kDa.
Figure 4:
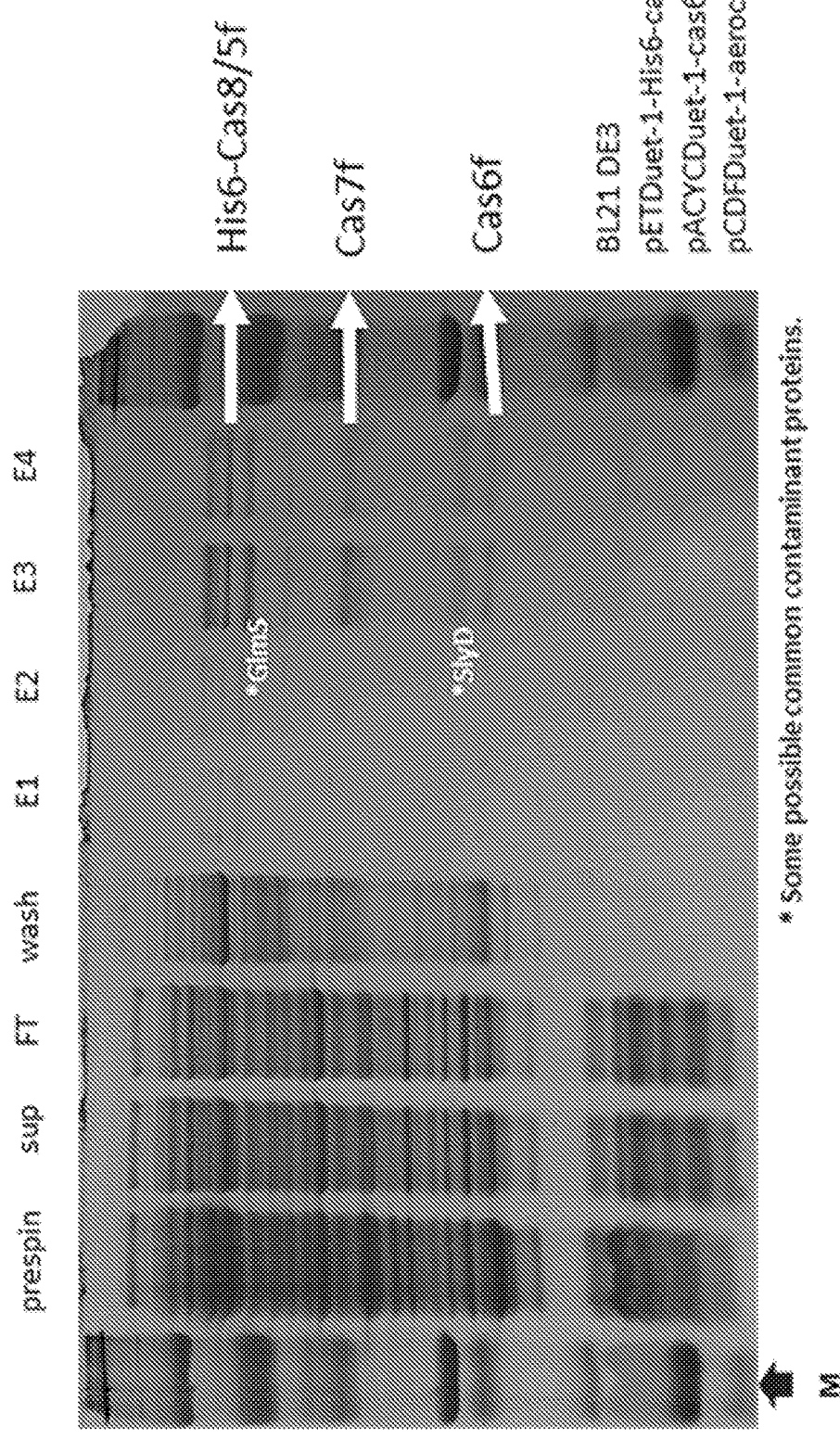
FIG. 4. Representative photograph of Immobilized Metal Ion Affinity Chromatography (IMAC) copurification of cascade complex. This figure demonstrates that by selectively isolating one of the components of the Cas complex and co-expressing the guide RNA, a complex with all three subunits is formed and can be pulled down using IMAC.
Figure 5:
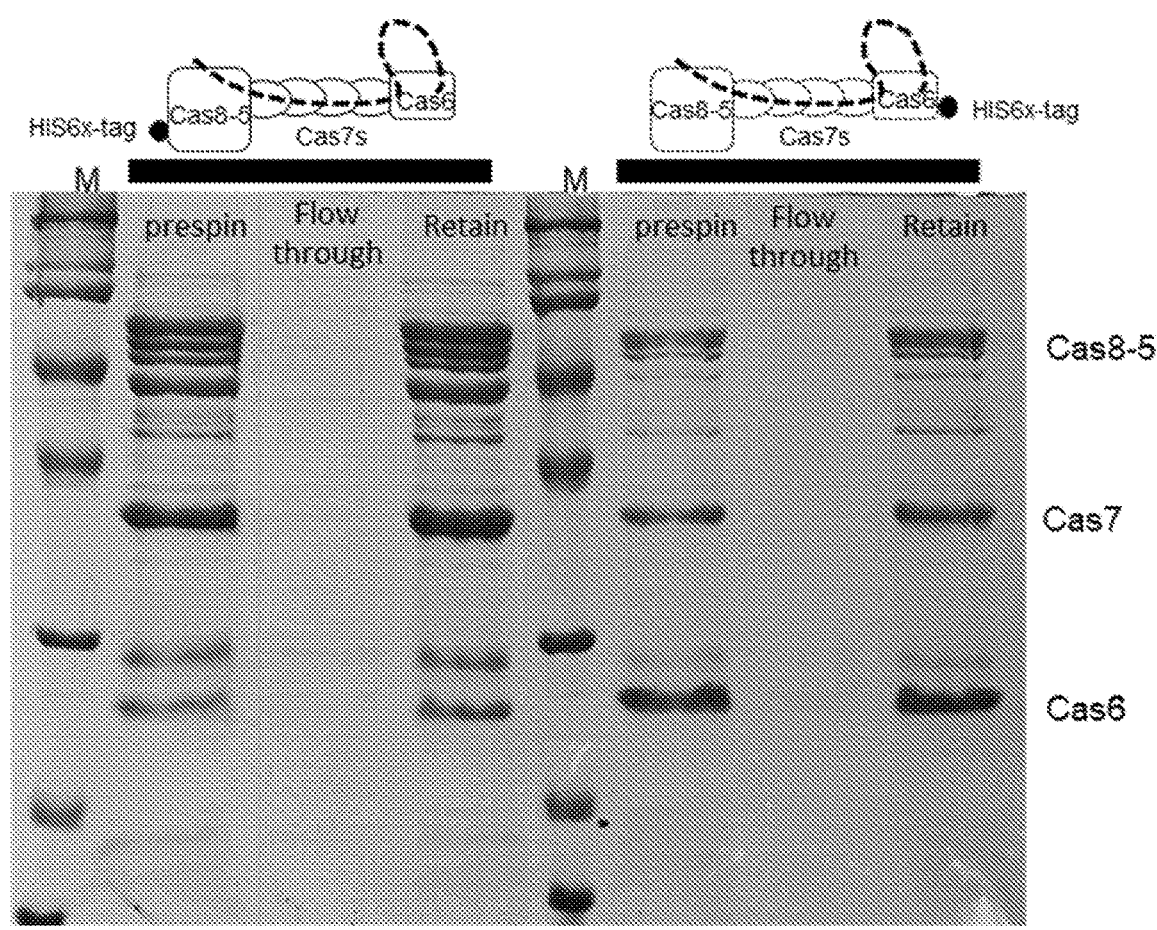
FIG. 5. Representative photograph of SDS-PAGE with Coomassie staining demonstrating that the Cas8-5, Cas7, Cas6, and guide RNA complex can be pulled down with an affinity tag either on Cas8-5 or on Cas6 and can be retained in a spin purification column with a molecular weight cut-off of 100 kiloDaltons. Complexes are shown above the image as cartoon representations.
Figure 6:
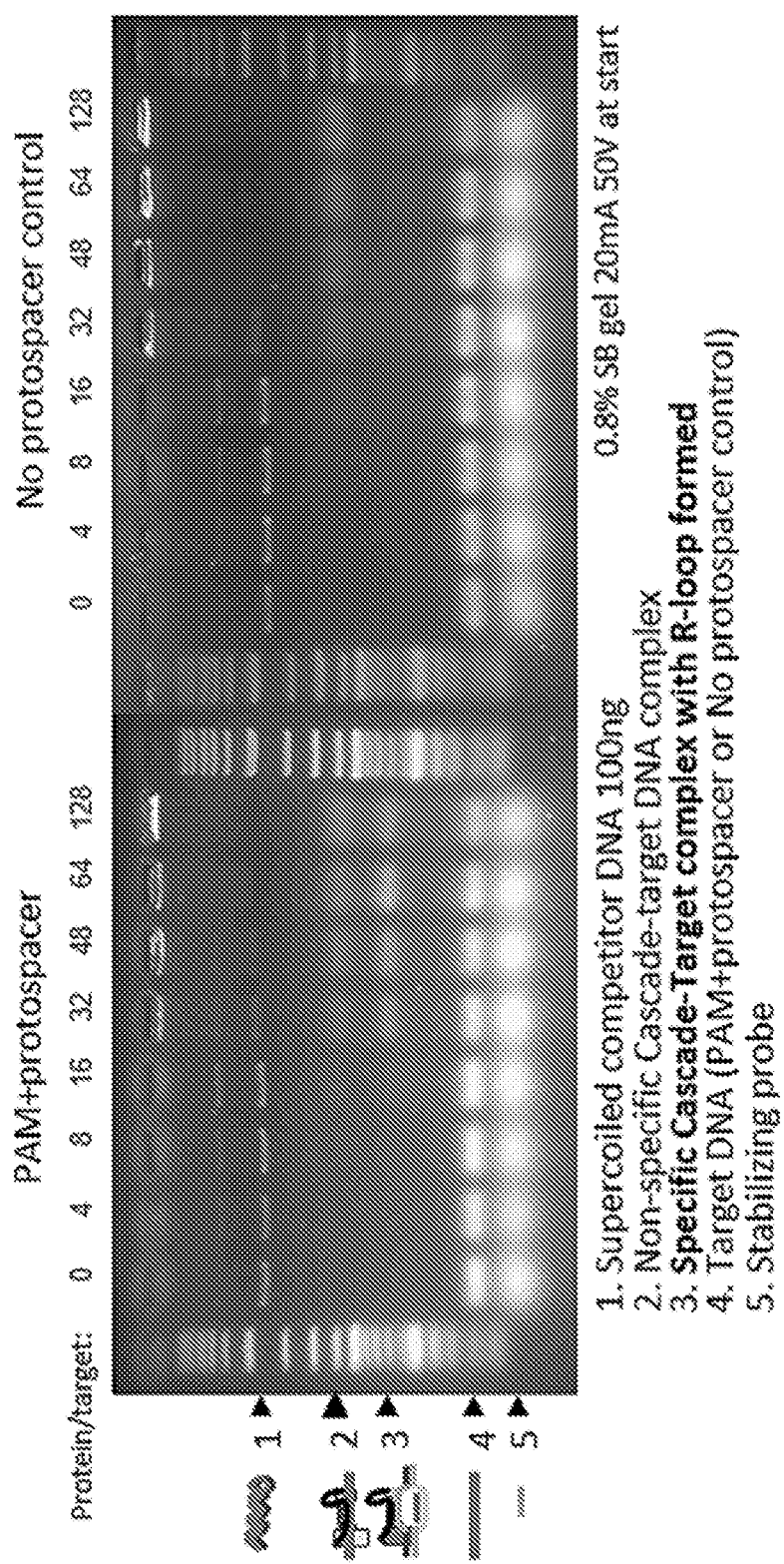
FIG. 6. Representative photograph of electrophoretic separation of DNA and protein complex with guide RNA and showing that a specific complex is found with target DNA with PAM+protospacer that is not found with a no protospacer control. To generate the results shown in the figure, a crude preparation Cas8-5, Cas7, Cas6-HIS6×, and guide RNA was incubated with a 200 bp double-stranded DNA target DNA (with or without the PAM+protospacer). A product that moves faster than the guide RNA complex with the PAM+protospacer indicates that an R-loop has formed, an important transition indicated the protospacer was fully recognized. This is not found with the "no protospacer" control. 100 ng of supercoiled plasmid DNA was added as a competitor for non-specific binding and an oligonucleotide specific to the displaced strand to help stabilize the complex. Products were separated in an agarose gel as indicated and stained with Ethidium Bromide for visualization.
Figure 7:
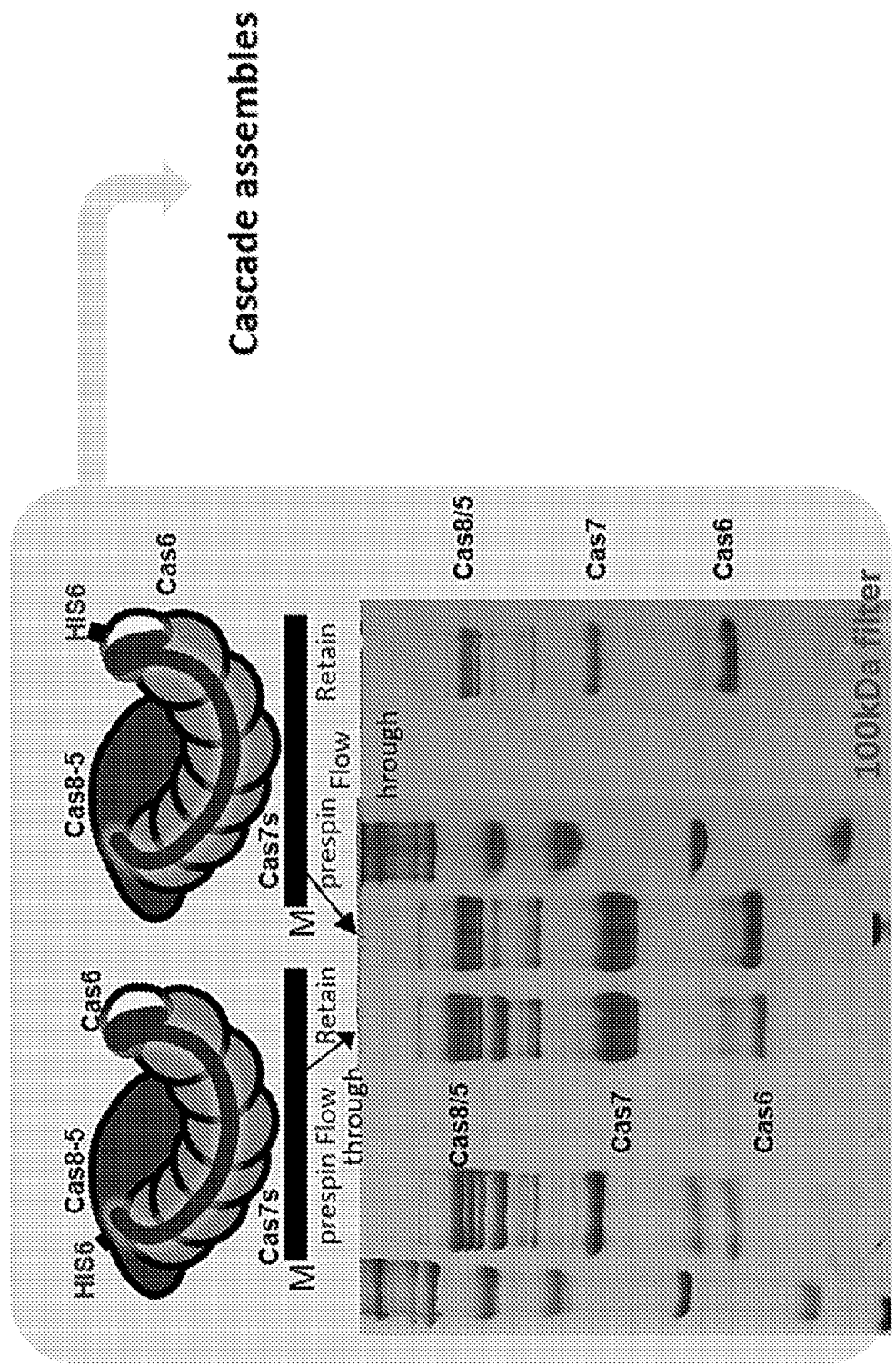
FIG. 7. Representative photograph of electrophoretic separation using SDS-PAGE with Coomossie staining. The results demonstrate that Cascade assembles and is stable as a complex when produced in *E. coli* in vitro. This demonstrates the CRISPR genes can process precrRNA and form cascade complex in heterologous host. Complexes are illustrated above the image as cartoons.
Figure 8:
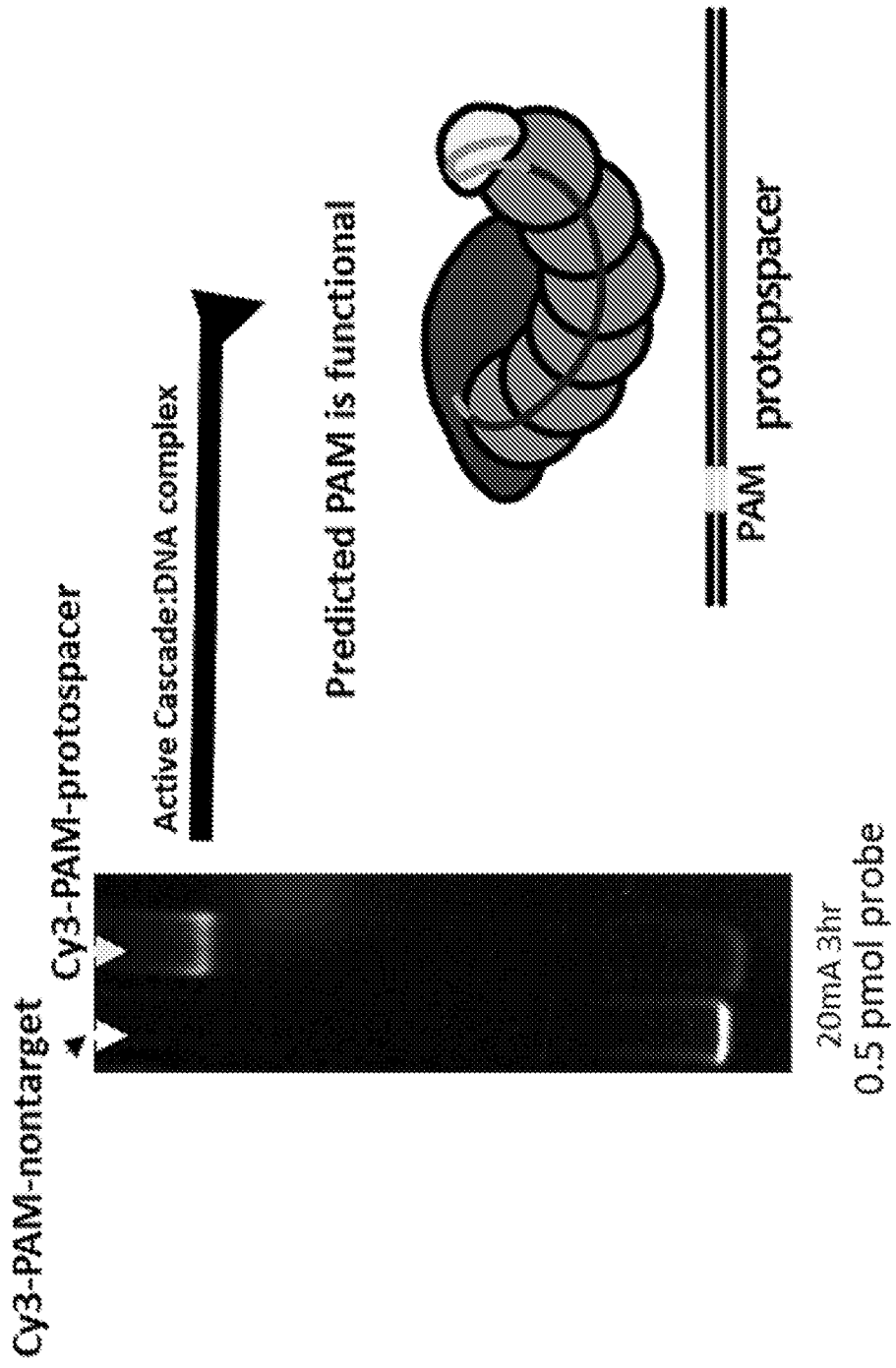
FIG. 8. Representative photograph of a mobility shift assay where the DNA substrate was visualized using a Cy3 fluorophore with excitation at the appropriate wavelength. The TniQ, Cas8-5, Cas7, Cas6 with guide RNA complex was incubated with a Cy3 labeled DNA substrate and then loaded onto a polyacrylamide gel to determine of the substrate was recognized and specifically bound. Only a substrate that included the PAM and protospacer was specifically recognized. The result shows that Cascade binds protospacer DNA specifically.
Figure 9:
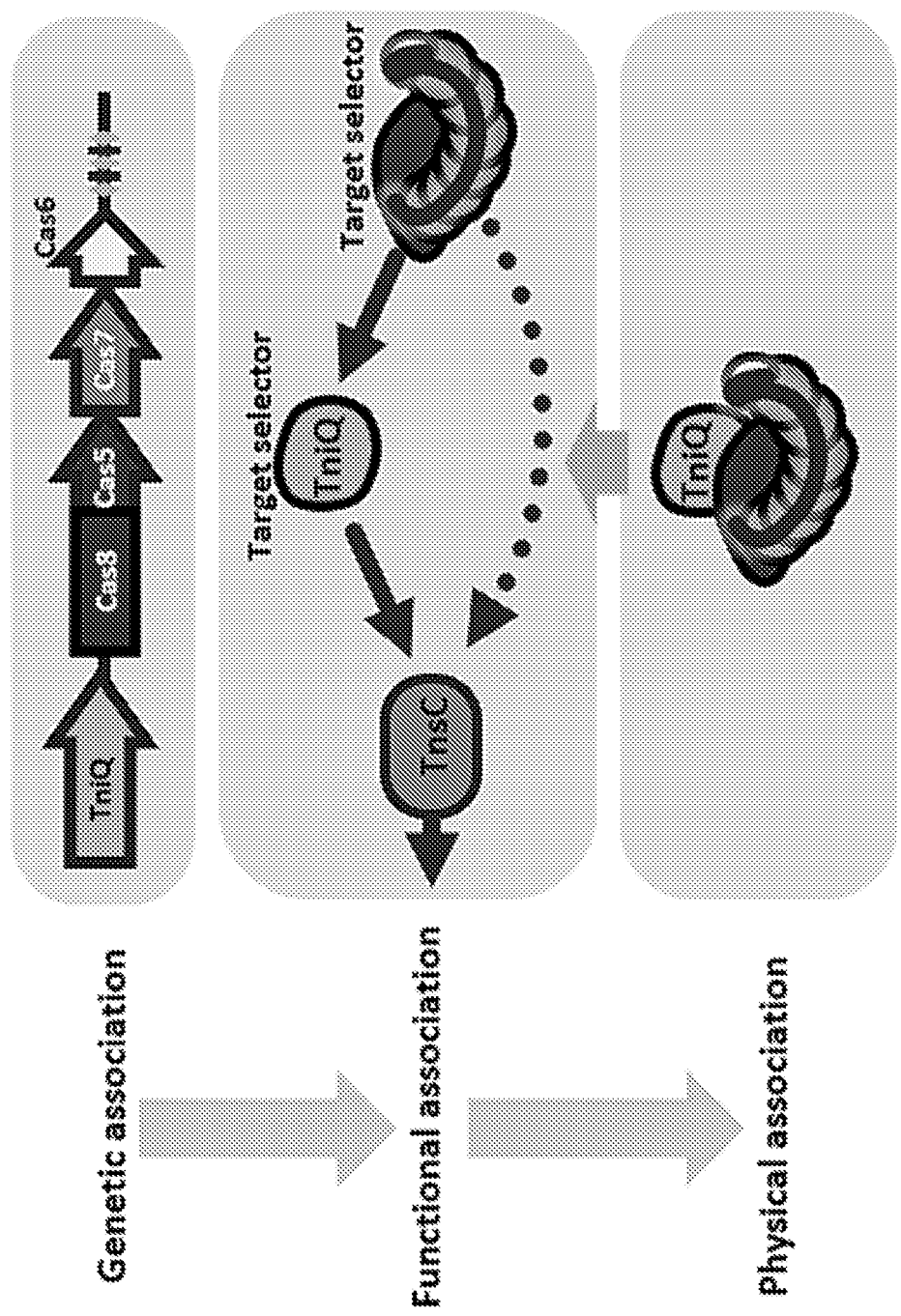
FIG. 9. Cartoon depiction of functional assay showing the contribution of TniQ.
Figure 10:
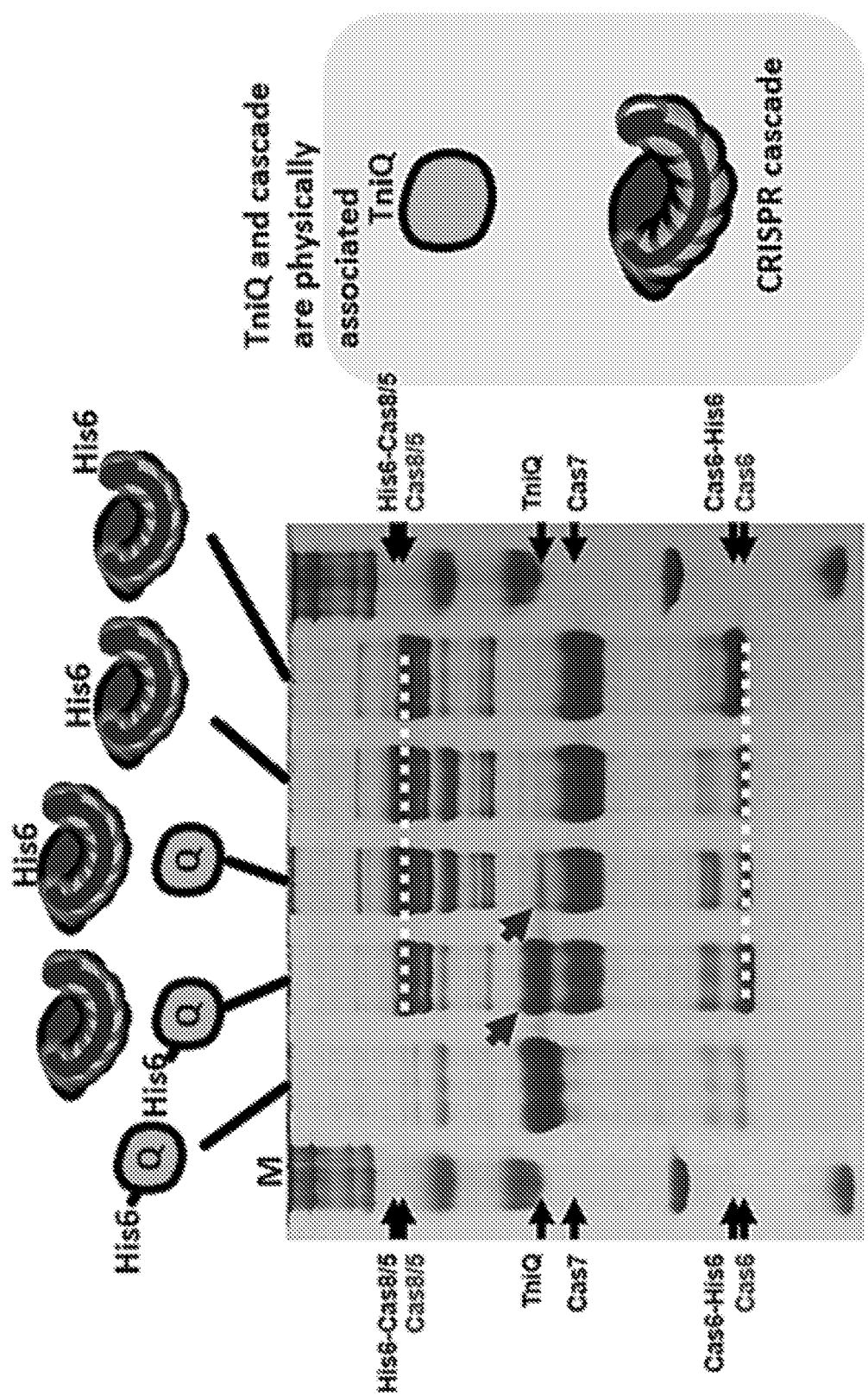
FIG. 10. Representative photograph of electrophoretic separation of complexes. The result shows that Cascade is stable as a complex as produced in *E. coli* and interacts with TniQ and can be separated out of solution using a HIS6 affinity tag. Dotted line indicates the altered position with and without the His6 affinity tag.
Figure 11:
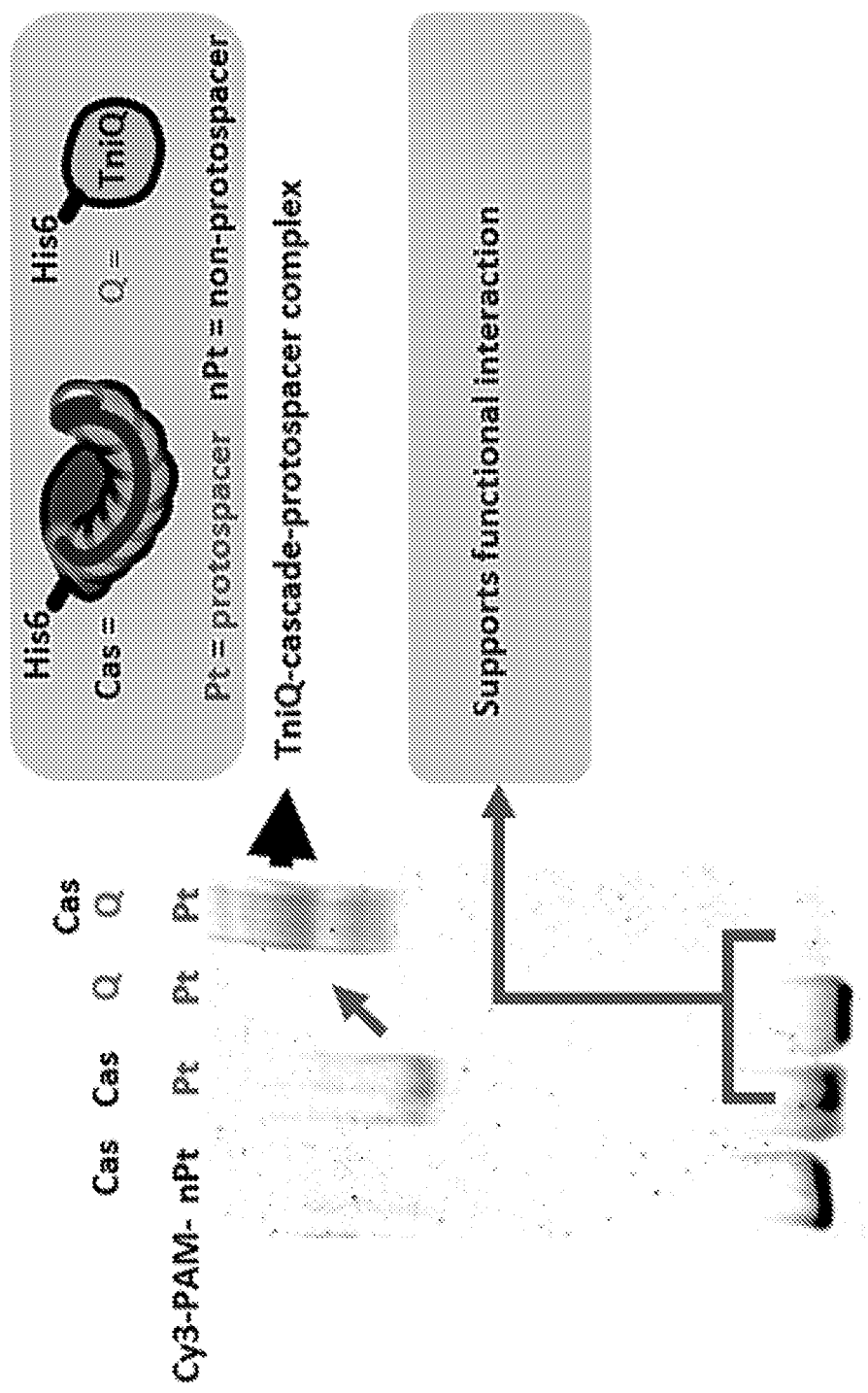
FIG. 11. Representative photograph of mobility shift assay as a functional assay showing that the behavior of the complex (Cas8-5,7,6) has more/better binding ability with TniQ. The results also show the complex specifically binds a protospacer target DNA (Pt), but not a randomly selected other DNA target (nPt). The gel represents a mobility shift assay on 3.5% sodium borate polyacrylamide gel, pH7.5. DNA substrates were visualized using a Cy3 fluorophore with excitation at the appropriate wavelength.
Figure 12:
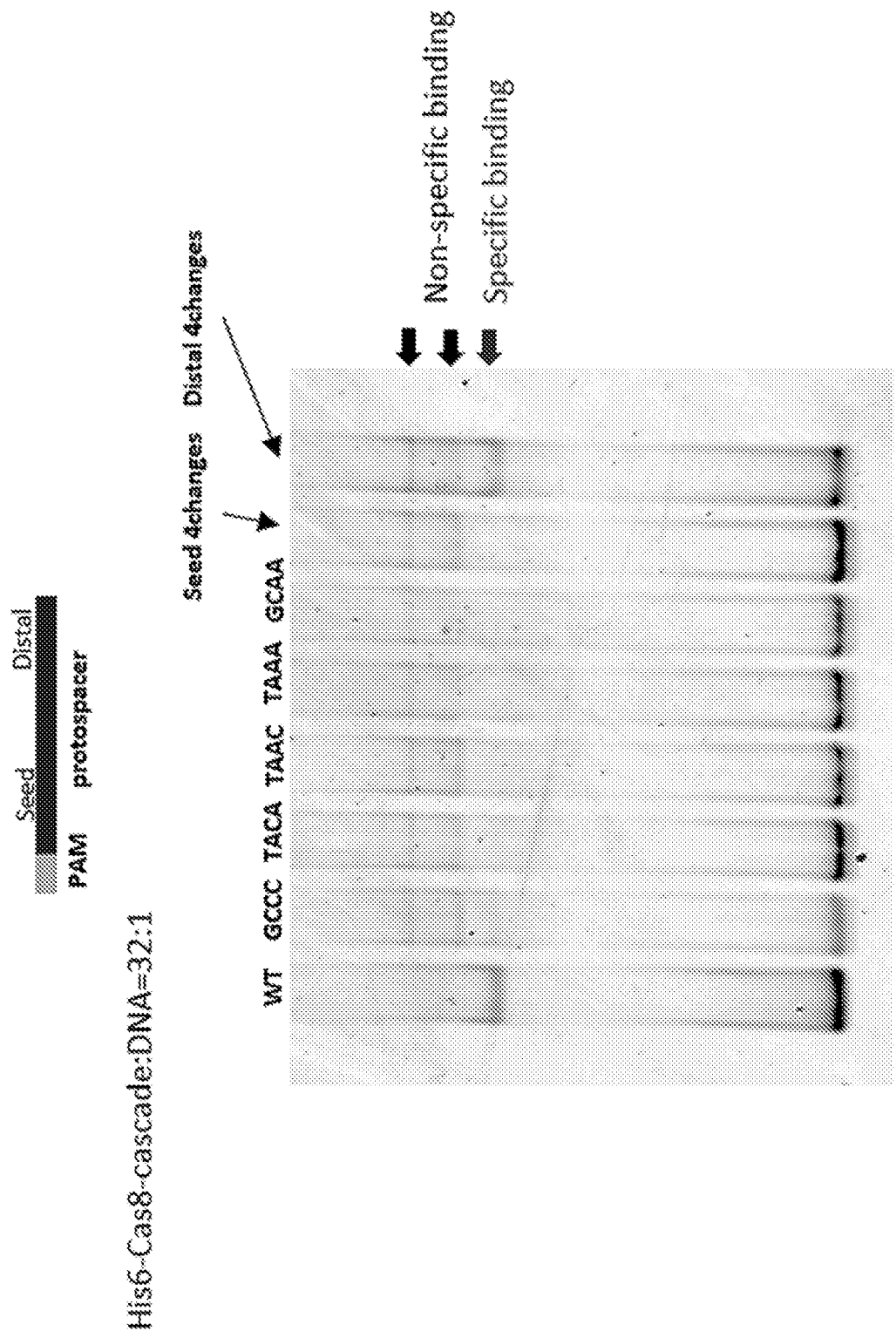
FIG. 12. Representative photograph of assay demonstrating specific and non-specific binding based on distinct PAM sequences. These results show that even the same guide RNA is only strongly recognized when the protospacer/spacer-match has the TACC (wt) PAM, but not the changes shown. The results also show that 4 mismatches/changes in the "seed" region (the region closer to the PAM) appear to not allow recognition, but 4 changes in the distal region more distant from the PAM appear to be tolerated. These results demonstrate strong specificity with the functioning with the guide RNA complex.
Figure 13:
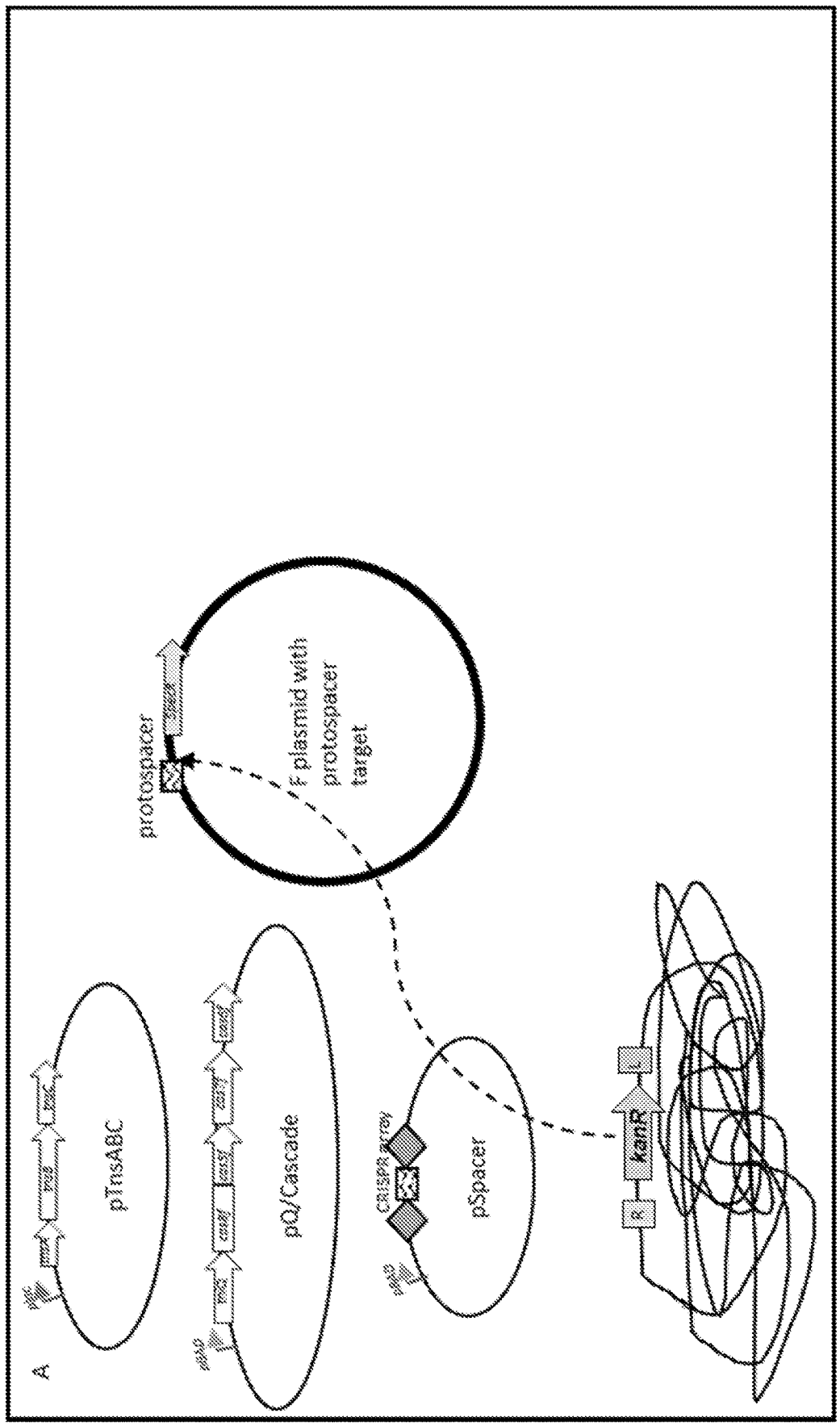
FIG. 13. Cartoon scheme of the transposition assay, and specifically depicting targeting of an F plasmid derivative with a candidate protospacer target. Expression plasmids contain TnsABC, TniQ/Cascade, and a synthetic CRISPR array. The donor element is a single copy inserted into chromosome. The figure shows the design of an experiment performed in a heterologous host (*E. coli*) as demonstrated in the Examples. The plac and pBAD are inducible promoters. The mini element is initially present in the *E. coli* chromosome, and guide RNA-directed transposition directed to the specific place next to the protospacer/spacer-match, which is measured by mating the conjugal/mobile F plasmid into another *E. coli* strain and the frequency determined (shown in FIG. 14).
Figure 14:
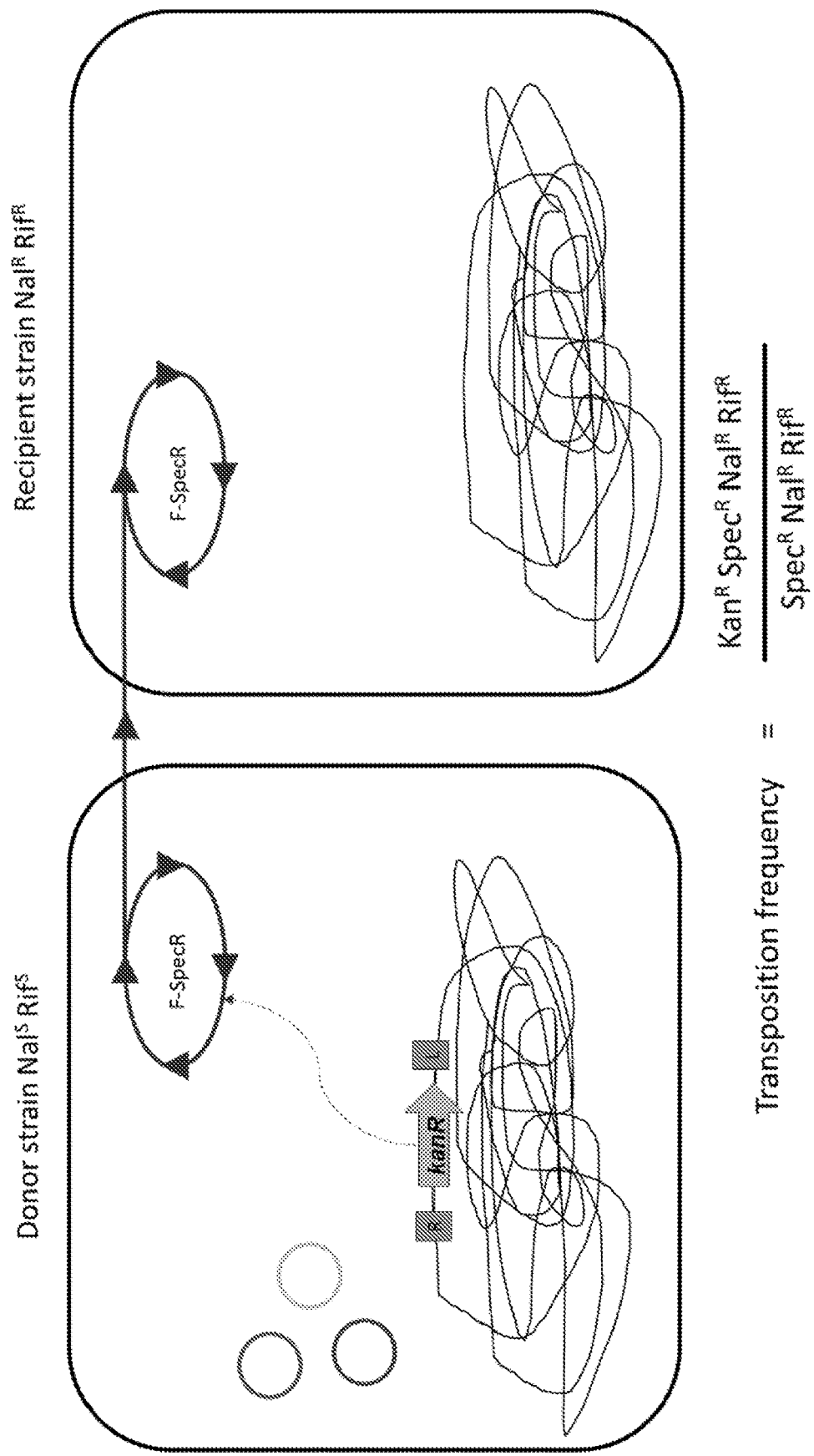
FIG. 14. Carton depiction, expanding on FIG. 13. The image depicts Guide RNA-directed transposition reconstituted in *E. coli* using an adaptation of a standard mate out assay. The image depicts how frequency of conjugal plasmids that now contain an insertion event are monitored by mating a population of cells post-induction with a Nal$^R$ Rif$^R$ recipient strain, followed by selection for recipient cells with the conjugal plasmid and mini element markers. In representative example, the full suite of transposition proteins resulted in thousands of colonies while the control lacking TnsABC had none. Frequency is estimated at least $10^{-2}$ in these conditions and has been determined to be higher, as described in the Examples.
Figure 15:
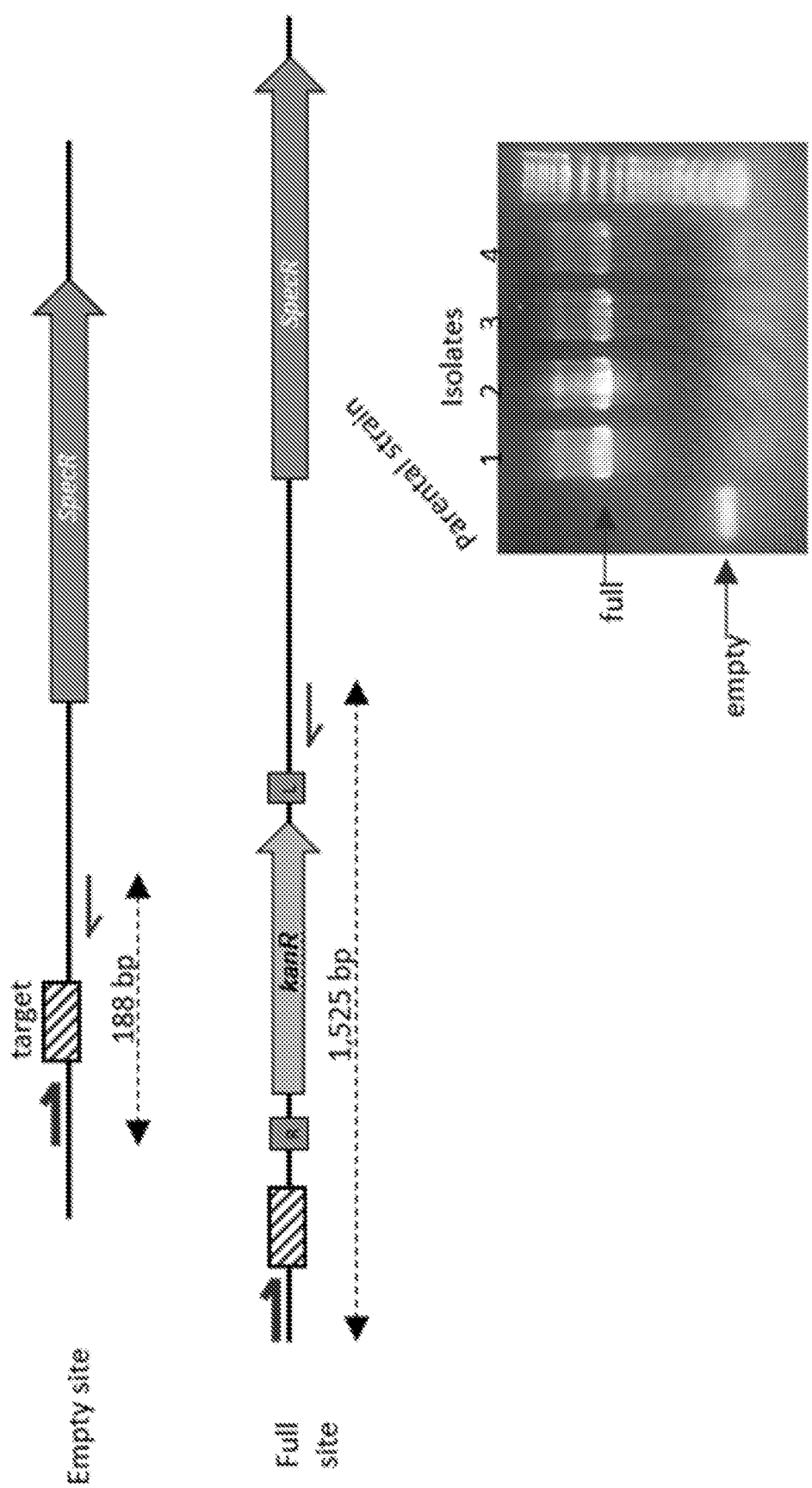
FIG. 15. Cartoon depiction of representative guide RNA-directed transposition reconstituted in *E. coli* with photographic representation of results. PCR across the predicted target site confirms transposition is not occurring elsewhere in the conjugal plasmid, but specifically next to the protospacer with 4 examples which were also sequenced. PCR with left and right end primers with 8 isolates were all in the correct orientation as predicted (not shown). DNA sequencing confirmed that all four insertions that were analyzed were correct with target site duplication found with transposition. Insertions were at 47, 48, 48, 49 bp from the protospacer. In this example, only protospacers+10 bp from *Aeromonas* is on each side in *E. coli*, demonstrating the insertions were made in new, engineered sequences in the heterologous host. The protospacer containing target is indicated with crosshatching. Antibiotic resistance makers for Kanamycin resistance (KanR) and Spectinomycin resistance (SpecR) used to identify the F plasmids with transposition events are indicted.

A non-limiting and general embodiment of the disclosure is depicted in FIG. 2. Each set of genes described herein can also include a suitable xre gene that encodes a transcription regulator. Further, any of the tns genes, as further described herein, may comprise mutations such that ns genes encode proteins that are distinct from the proteins that are produced in nature, i.e., proteins that are produced by bacteria that have not been engineered to produce a modified Tns protein.

In particular, any cell of interest can be adapted to express the transposon and Cas proteins. For bacteria, this can be from an independently replicating plasmid or bacteriophage DNA or other element, or a vector that integrates into the genome, or an alternative delivery vector that is maintained or not maintained afterwards. In one embodiment, the user designs a guide RNA that matches the sequences adjacent to the desired point of insertion. Suitable approaches for designing guide RNAs are established and take into account any sequence requirements that are dictated by any adjacent motifs (called PAM sequences). This guide RNA is cloned into a delivery vector between the CRISPR array repeats (see, for example, FIG. 2, panel B). Any guide RNA used in embodiments of this disclosure can comprise RNA sequences which comprise RNA equivalents of all or portions of repeat sequences. In embodiments, a guide RNA of this disclosure may be processed by one or more proteins described herein. In embodiments, the guide RNA is processed from a longer RNA polynucleotide that comprises, for example, at least one repeat-spacer-repeat segment. More than one such segment may be included in the RNA that is processed into the guide RNA, and each processed guide RNA may be configured to target the same DNA sequence, or distinct DNA sequences.

The disclosure includes using a least one tniQ gene, and accordingly two or more different tniQ genes may be used. tniQ genes produce a TniQ protein that is an optional part of the present system. Including this gene in the construct will direct transposition event into the one specific cognate site recognized by the TniQ protein. Without intending to be bound by any particular theory, it is considered that TniQ may also interact with the CRISPR/Cas and be required for guide RNA targeting. The genes of interest that are to be delivered into the bacterial strain are cloned into a multi-cloning site (MCS) in the delivery vector using existing standard lab techniques (FIG. 2, panel B). The MCS is located between the left (L) and right (R) synthetic transposon end-sequences. If orientation of the final insertion is important for a particular embodiment, the right end of the element will be proximal to the match to the selected guide RNA. The delivery vector can be designed as a conditional vector that will not be maintained if desired. If desired, a selectable genetic marker can also be included in this vector. If the delivery vector will not be maintained, integration of the DNA by the targeted transposition process can be directly selected. If the efficiency is high enough, then this selectable marker is not needed.

This system can also be used to inactivate any gene in a prokaryotic or eukaryotic genome. Any one of many selectable markers can be included in the delivery vector to allow inactivation of a gene targeted by the guide RNA. This type of technology is broadly applicable to engineering new bacterial strains and eukaryotic cells for industry, research and therapeutic applications.

In contrast to existing CRISPR-based editing techniques, one advantage of the present systems is that no separate DNA break is used; instead the DNA fragment of interest is directly joined into the genome at one position determined by the user.

In non-limiting demonstrations, the disclosure shows that systems described herein, and which include recombinantly produced proteins (the Cas proteins with or without TniQ are referred to in certain instances as 'cascade") can specifically recognize and bind to a DNA substrate that comprises a protospacer. As used in certain examples, cascade comprises Cas8-5 (encoding fused Cas proteins), Cas7, Cas6 and a guide RNA with or without one or more TniQ proteins. This combination illustrates cascade for variant I-F systems associated with Tn7-like elements.

For example, as shown in the examples and figures of this disclosure, in vitro binding of cascade occurs with specificity to a DNA substrate comprising a protospacer, to which the cascade complex is directed using a suitable guide RNA. Likewise, the figures and examples demonstrate copurification of a complex comprising TniQ and cascade. Thus, the disclosure shows that recombinantly produced TinQ and cascade form a physical association. Moreover, the disclosure demonstrates functionality of the system in a living heterologous system (illustrated using *E. coli*). In particular, at least FIG. 16 and Example 2, show guided transposition that is specific for a particular location in a conjugal plasmid, and that this transposition is PAM specific. In particular, in endogenous *Aeromonas*, the insertion was 48 base pairs from the protospacer. In the heterologous *E. coli* system, four insertions analyzed were 47, 48, 48, and 49 base pairs away from the protospacer, demonstrating an unexpected degree of precision in a heterologous system. Thus, the disclosure demonstrates functionality of the system using recombinant approaches in living cells that do not, without modification as described herein, produce a directed transposition event. Additionally, the disclosure demonstrates transposition from one location in a chromosome to another location in the chromosome, as shown in FIG. 17, and described in Example 3, results which are also obtained in a heterologous system, using *E. coli* as a representative example.

In embodiments, systems of this disclosure include a DNA cargo for insertion into a eukaryotic chromosome or extrachromosomal element, or in the case of prokaryotes, a chromosome or a plasmid. Thus, instead of transposing an existing segment of a genome in the manner in which transposons ordinarily function, the disclosure provides for insertion of DNA cargo that can be selected by the user of the system. The DNA cargo may be provided, for example, as a circular or linear DNA molecule. The DNA cargo can be introduced into the cell prior to, concurrently, or after introducing a system of the disclosure into a cell. The sequence of the DNA cargo is not particularly limited, other than a requirement for suitable right and left ends that are recognized by proteins of the system. The right and left end sequences that are required for recognition are typically from about 90-150-bp in length. As is known in the art, such 90-150 bp length comprises multiple 22 bp binding sites for the TnsB transposase in the element in each of the ends that can be overlapping or spaced. The minimum length of the DNA cargo is typically about 700 bp, but it is expected that from 700 bp to 120 kb can be used and inserted. The disclosure provides for insertion of a DNA cargo without making a double-stranded break, and without disrupting the existing sequence, except for several residual nucleotides at the insertion site, as is known in the art for transposons. In embodiments, the insertion of the DNA cargo occurs at a position that is from approximately 47, 48, or 49 nucleotides from a protospacer in the target (e.g., chromosome or plasmid) sequence.

In embodiments, the transposable DNA cargo sequence is transposed into the chromosome or extrachromosomal element within a 5 nucleotide sequence that includes the nucleotide that is located 47 nucleotides 3' relative to the 3' end of the protospacer. In embodiments, a DNA cargo insertion comprises an insertion at the center of a 5 bp target site duplication (TSD). Thus, by providing a suitable guide RNA that comprises a PAM that is cognate to the protospacer, precise integration of a DNA cargo can be achieved. In embodiments, the PAM comprises or consists of TACC or CC.

The transposon and Cas genes can be expressed from any of a wide variety of existing mechanism that can replicate separately in the cell or be integrated into the host cell genome. Alternatively, they could be expressed transiently from an expression system that will not be maintained. It is expected that the proteins themselves could be directly transformed into the host strain to allow their function. The disclosure allows for multiple copies of distinct transposon gene cassettes, multiple copies of Cas genes, CRISPR arrays, and multiple distinct cargo coding sequences to be introduced and to modify genetic material in the same cell. In embodiments a first set of transposon genes tnsA, tnsB, tnsC, and optionally one or more tniQ genes, Cas genes cas8f, cas5f cas7f, and cas6f and an xre gene, and a sequence encoding at least a first guide RNA that is functional with proteins encoded by the Cas genes, wherein at least one of the first set of transposon genes, the Cas genes, or the sequence encoding the first guide RNA are present within and/or are encoded by a recombinant polynucleotide that is introduced into bacteria, or eukaryotic cells. The disclosure thus includes second, third, fourth, fifth, or more copies of distinct transposon genes, Cas genes, and distinct cargo coding sequences.

The delivery vector can be based on any number of plasmid, bacteriophage or another genetic element, when used in prokaryotes. The vector can be engineered so it is maintained, or not maintained (using any number of existing plasmid, bacteriophage or other genetic elements). Delivery of these DNA constructions in bacteria can be by conjugation, bacteriophage or any transformation processes that functions in the bacterial host of interest. Modifications of this system may include adapting the expression system to allow expression in eukaryotic or archaeal hosts. In embodiments, for eukaryotic cells, the disclosure includes use of at least one nuclear localization signal (NLS) in one or more proteins. In general, a suitable NLS includes one or more short sequences of positively charged lysines or arginines exposed on the protein surface. In embodiments, a system of this disclosure is introduced into eukaryotic cells using, for example, one or more expression vectors, or by direct introduction of ribonucleoproteins (RNPs). In embodiments, expression vectors comprise viral vectors. In an embodiment, adenoviral vectors may be used, and many such vectors are known in the art.

Further modification of this approach can include expression and isolation of the proteins required for this process and carrying out some or all of the process in vitro to allow the assembly of novel DNA substrates. These DNA substrates can subsequently be delivered into living host cells or used directly for other procedures. Thus, the disclosure includes compositions, methods, vectors, and kits for use in the present approach to CRISPR—Transposon based editing.

In one example, the disclosure provides a system for modifying a genetic target in bacteria and/or eukaryotic cells. The system comprises a first set of transposon genes tnsA, tnsB, tnsC, and optionally one or more tniQ, Cas genes cas8f cas5f cas7f and cas6f, and an xre gene encoding a transcription regulator, and a sequence encoding a first guide RNA that is functional with proteins encoded by the Cas genes, wherein at least one of the first set of transposon genes, the Cas genes, and/or or the sequence encoding the first guide RNA are present within and/or are encoded by a recombinant polynucleotide. Without intending to be constrained by any particular theory, it is considered that the xre gene, while annotated as a transcriptional regulator, can also make transposition complexes described herein more efficient.

In embodiments, one or more of the tns genes, and therefore the proteins they encode, are modified, as described in more detail below. From this disclosure, and other information known to those skilled in the art, homologous proteins can be recognized, aligned, and amino acid changes in the proteins can be made such that the proteins function in a manner similar to those described herein. All such homologous proteins and mutations thereof are included in this disclosure. The disclosure also includes combinations of naturally occurring genes and proteins, with the exception that one or more of the naturally occurring sequences may be expressed from one or more recombinant vectors. In embodiments, combinations of naturally occurring proteins, wherein the proteins are from distinct sources, are used. In embodiments, homologous proteins are from any bacteria, including but not limited to Proteobacteria. Certain embodiments of mutations in proteins that are included in the disclosure are provided below. The mutations can be in any one or any combination of proteins encoded by the tnsA gene, the tnsB gene, and the tnsC gene.

In embodiments, the Tns proteins that are provided by this disclosure comprise mutations relative to a wild type sequence. A "wild type" sequence as used herein means a sequence that preexists in nature without experimentally engineering a change in the sequence. In embodiments, a wild type sequence is the sequence of a transposition element, a non-limiting example of which is the sequence of *Aeromonas salmonicida* strain S44 plasmid pS44-1, which can be accessed via accession no. CP022176 (Version CP022176.1), such as via https://www.ncbi.nlm.nih.gov/nuccore/CP022176.

In embodiments, the mutations described in i), ii) and iii) below provide for an increase in transposition frequency that is similar or greater than a value obtained from a control construct. In embodiments, the control construct comprises one or more Tns genes in which a mutation described herein is not present. In embodiments, a control transposition frequency is a frequency exhibited by a transposition element from *Aeromonas hydrophila* strain AFG_SD03, which can be identified from Accession PUTQ01000019 (Version PUTQ01000019.1), and which comprises representative amino acid sequences described below, except for the indicated mutations. The pertinent sequence of *Aeromonas hydrophila* strain AFG_SD03 can be accessed via, for example, www.ncbi.nlm.nih.gov/nuccore/1427716682. The *Aeromonas salmonicida* Cas8/5 amino acid sequence is available under accession number ASI25653, www.ncbi.nlm.nih.gov/protein/ASI25653.1; *Aeromonas salmonicida* Cas7 amino acid sequence is available under accession number ASI25654, www.ncbi.nlm.nih.gov/protein/ASI25654.1; *Aeromonas salmonicida* Cas6 amino acid sequence is available under accession number ASI25655, www.ncbi.nlm.nih.gov/protein/ASI25655.1

In embodiments, for instance in bacteria, transposition frequency can be determined using, for example, a bacteriophage (i.e. viral) vector that cannot replicate or integrate into the bacterial strain used in the assay. Therefore, while the viral vector injects its DNA into the cell, it is lost during cell replication. Encoded in the phage DNA is a miniature Tn7 element where the Right and Left ends of the element flank a gene that encodes resistance to an antibiotic, such as Kanamycin (KanR). If the transposon remains on the bacteriophage DNA the cell will still be killed by the antibiotic because the bacteriophage cannot be maintained in that particular strain of bacteria. However if the TnsA, TnsB, TnsC and other required transposon proteins and nucleotide sequences described herein are added to the cell, transposition will occur because the transposon can move from the bacteriophage DNA into the chromosome (or plasmid) where it will be maintained and allow a colony of bacteria to grow that is antibiotic resistant. Therefore, when the number of infectious bacteriophage particles are in the assay is known, it permits calculation of a frequency of transposition as antibiotic resistant colonies of bacteria per bacteriophage used in the experiment. Thus, in embodiments, using one or a combination of the mutated proteins described herein increases transposition frequency, and accordingly is expected to enhance CRIPSR mediated cleavage that is accompanied by the transposon-based constructs that are described herein. In alternative embodiments, detectable markers and selection elements can be used. In embodiments, transposition frequency can be measured, for example, by a change in expression in a reporter gene. Any suitable reporter gene can be used, non-limiting examples of which include adaptations of standard enzymatic reactions which produce visually detectable readouts. In embodiments, adaptations of β-galactosidase (LacZ) assays are used. In embodiments, transposition of an element from one chromosomal location to another, or from a plasmid to a chromosome, or from a chromosome to a plasmid, results in a change in expression of a reporter protein, such as LacZ. In embodiments, use of a system described herein causes a change in expression of LacZ, or any other suitable marker, in a population of cells. In embodiments, transposition efficiency is determined by measuring the number of cells within a population that experience a transposition event, as determined using any suitable approach, such as by reporter expression, and/or by any other suitable marker and/or selection criteria. In embodiments, the disclosure provides for increased transposition, such as within a population of cells, relative to a control. The control can be any suitable control, such as a reference value. In embodiments, the reference value comprises a standardized curve(s), a cutoff or threshold value, and the like. In embodiments, transposition efficiency comprises use of a system of this disclosure to transpose all or a segment of DNA from one location to another within the same or separate chromosomes, from a chromosome to a plasmid, or from a plasmid or other DNA cargo to a chromosome. In embodiments, transposition efficiency is greater than a control value obtained or derived from transposition efficiency using the described system, but wherein the TnsA protein comprises the wild type sequence, i.e., wherein the TnsA transposon protein comprises SEQ ID NO:1, including the Alanine at position 125. In embodiments, the increased transposition efficiency using a wild type TnsA protein (i.e., a TnsA protein comprising SEQ ID NO:1) is undetectable in the same type of assay wherein a described TnsA mutant protein is used.

In embodiments, assuming only for illustration, a frequency of transposition of 0.0001% is a control value because transposition efficiency was not able to be measured in the representative assays, (e.g., hypothetically only one in 100,000 cells into which a presently described system using a wild type TnsA protein experience a transposition event). In this regard, the present disclosure provides for a 1 fold to 200 fold increase in transposition efficiency, inclusive, and including all numbers and ranges of to the first decimal point there between. In embodiments, the disclosure facilitates an increase of transposition efficiency relative to a control, such as transposition from a chromosome to a plasmid, of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, fold greater than a control value. Representative examples of assays wherein transposition frequency can be determined are described at least in FIG. 13 through FIG. 17. Similar transposition efficiency can be determined for transposition events where the transposition comprises transposing an element in cis, e.g., transposition from one location in a chromosome to a different location in the same chromosome. Representative results using this approach are shown in FIG. 17 and are described in at least Example 3.

i) In one embodiment of this disclosure, the tnsA gene comprises a change in sequence such that at least one amino acid in the TnsA protein encoded by the tnsA gene is changed relative to its wild type sequence. In an embodiment, the change in the TnsA protein comprises a change of Ala at position 125 of an *Aeromonas salmonicida* TnsA protein, wherein optionally the change is to an Asp, or is a homologous change in a homologous TnsA protein. A representative TnsA amino acid sequence is provided below. In this regard, we have demonstrated that this construct can introduce numerous insertions, but without the change insertions approximate background levels, or are undetectable.

ii) In embodiments, the disclosure includes a tnsB gene comprising a change in sequence such that at least one amino acid in the TnsB protein encoded by the tnsB gene is changed relative to its wild type sequence. In an embodiment, the change in the TnsB protein comprises a change of amino acid position 167 of an *Aeromonas salmonicida* TsnB protein, wherein optionally the change is a Ser, or is a homologous change in a homologous position of a homologous TnsB protein. Representative TnsB amino acid sequences are provided below.

iii) As with the TnsA and TnsB proteins, in embodiments, the disclosure includes a modified tnsC gene that comprises a change in sequence such that at least one amino acid in the TnsC protein encoded by the tnsC gene is changed relative to its wild type sequence. In embodiments, the change is optionally located in a TnsC Walker B motif. In embodiments, the change in a Walker B motif is, for example, in position 135, 136, 137, 138, 139, or 140 of the *Aeromonas salmonicida* TnsC protein, a representative example of which is shown below. In one embodiment, the change is to an amino acid at position 140 in the TnsC protein, wherein, for example, amino acid 140 is change to an Ala or Gln, or a homologous change in a homologous position of a homologous TnsC protein is made.

iv) the tnsC gene comprises a change in sequence such that at least one amino acid in the TnsC protein encoded by the tnsC gene is changed relative to its wild type sequence, wherein the change is optionally in a TnsC Walker B motif.

In embodiments, any composition, system, or method of this disclosure may be performed in the absence of any TnsE transposon protein. TnsE transposon proteins are known in the art. In a non-limiting embodiment, any composition, system, and/or method of this disclosure may be performed in the absence of, and/or without participation of, an *E. coli* TnsE protein that comprises or consists of the following amino acid sequence:

MVRLATFNDNVQVVHIGHLFRNSGHKEWRIFVWFNPMQERKWTRFTHLPL

LSRAKVVNSTTKQINKADRVIEFEASDLQRAKIIDFPNLSSFASVRNKDG

AQSSFIYEAETPYSKTRYHIPQLELARSLFLINSYFCRSCLSSTALQQEF

DVQYEVERDHLEIRILPSSSFPKGALEQSAVVQLLVWLFSDQDVMDSYES

IFRHYQQNREIKNGVESWCFSFDPPPMQGWKLHVKGRSSNEDKDYLVEEI

VGLEINAMLPSTTAISHASFQEKEAGDGSTQHIAVSTESVVDDEHLQLDD

EETANIDTDTRVIEAEPTWISFSRPSRIEKSRRARKSSQTILEKEEATTS

ENSNLVSTDEPHLGGVLAAADVGGKQDATNYNSIFANRFAAFDELLSILK

TKFACRVLFEETLVLPKVGRSRLHLCKDGSPRVIKAVGVQRNGSEFVLLE

VDASDGVKMLSTKVLSGVDSETWRNDFEKIRRGVVKSSLNWPNSLFDQLY

GQDGHRGVNHPKGLGELQVSREDMEGWAERVVREQFTH.

In embodiments, any composition, system, and/or method of this disclosure may be performed in the absence of, and/or without participation of any TnsE protein that is a homologue of the foregoing sequence, but is from a type of bacteria that is not *E. coli*. Non-limiting embodiments of amino acid sequences comprising mutations and/or locations of mutations are described herein, and by way of the following amino acid sequences and accession numbers. Enlarged, bold and italicized amino acids signify non-limiting examples of mutations that are encompassed by this disclosure. Enlarged sequences are locations where other mutations may be made, and are also included in this disclosure:

TnsA (A125D) change from *Aeromonas salmonicida* strain S44 plasmid pS44-1 or TnsA (exact from *Aeromonas hydrophila* strain AFG_SD03)
(SEQ ID NO: 1)
MYRRHLKHSRVKNLFKFVSAKMNTVFTVESALEFDTCFHLEYSPSVKFY

EAQPEGFYYEFAGRQCPYTPDFRLVDQNDSVSFLEIKPSDKVADPDFLH

RFPLKQQRAIELSSPLKLVTEKQIRI*D*PILGNLKLLHRYSGFQSFTPLH

MQLLGLVQKLGRVSLLRLSDSIDAPPEEVLASALSLIARGIMQSDLTVQ

KIGISSFVWAGGHSGIDHG

TnsA (A125) TnsA from *Aeromonas salmonicida* strain S44 plasmidp S44-1
(SEQ ID NO: 2)
MYRRHLKHSRVKNLFKFVSAKMNTVFTVESALEFDTCFHLEYSPSVKFY

EAQPEGFYYEFAGRQCPYTPDFRLVDQNDSVSFLEIKPSDKVADPDFLH

-continued

RFPLKQQRAIELSSPLKLVTEKQIRAPILGNLKLLHRYSGFQSFTPLHM

QLLGLVQKLGRVSLLRLSDSIDAPPEEVLASALSLIARGIMQSDLTVQK

IGISSFVWAGGHSGIDHG

TnsB (from *Aeromonas salmonicida* strain S44 plasmid pS44-1)

(SEQ ID NO: 3)
MDKHNGGLFEDEFVIPQPSTSTSPIDAIQAVLPATVDSFPYVLKVEALH

RRDYILWVEKNLAGGWTEKNLTPLLADAALVLPPPTPNWRTLARWRKIY

IQHGRKLVSLIPKHQAKGNARSRLPPSDELFFEQAVHRYLVGEQPSIAS

AFQLYSDSIRIENLGVVENPIKTISYMAFYNRIKKLPAYQVMKSRKGSY

IADVEFKAIASHKPPSRIMERVEIDHTPLDLLLLDDDLLVPLGRPSLTL

LIDAYSHCVVGFNLNFNQPSYESVRNALLSSISKKDYVKNKYPSIEHEW

PCYGKPETLVVDNGVEFWSASLAQSCLELGINIQYNPVRKPWLKPMIER

MFGIINRKLLEPIPGKTFSNIQEKGDYDPQKDAVMRFSTFLEIFHHWVI

DVYHYEPDSRYRYIPIISWQHGNKDAPPAPIIGDDLTKLEVILSLSLHC

THRRGGIQRYHLRYDSDELASYRMNYPDQTRGKRKVLVKLNPRDISYVY

VFLEDLGSYIRVPCIDPIGYTKGLSLQEHQINVKLHRDFINEQMDVVSL

SKARIYLNDRIKNELIEVRRNIRQRNVKGVNKIAKYRNVGSHAETSIVH

ELNHPATNEVISKMESASQPEHCDDWDNFTSGLEPY

TnsB (P167S) change from *Aeromonas salmonicida* strain S44 plasmid pS44-1

(SEQ ID NO: 4)
MDKHNGGLFEDEFVIPQPSTSTSPIDAIQAVLPATVDSFPYVLKVEALH

RRDYILWVEKNLAGGWTEKNLTPLLADAALVLPPPTPNWRTLARWRKIY

IQHGRKLVSLIPKHQAKGNARSRLPPSDELFFEQAVHRYLVGEQPSIAS

AFQLYSDSIRIENLGVVENSIKTISYMAFYNRIKKLPAYQVMKSRKGSY

IADVEFKAIASHKPPSRIMERVEIDHTPLDLLLLDDDLLVPLGRPSLTL

LIDAYSHCVVGFNLNFNQPSYESVRNALLSSISKKDYVKNKYPSIEHEW

PCYGKPETLVVDNGVEFWSASLAQSCLELGINIQYNPVRKPWLKPMIER

MFGIINRKLLEPIPGKTFSNIQEKGDYDPQKDAVMRFSTFLEIFHHWVI

DVYHYEPDSRYRYIPIISWQHGNKDAPPAPIIGDDLTKLEVILSLSLHC

THRRGGIQRYHLRYDSDELASYRMNYPDQTRGKRKVLVKLNPRDISYVY

VFLEDLGSYIRVPCIDPIGYTKGLSLQEHQINVKLHRDFINEQMDVVSL

SKARIYLNDRIKNELIEVRRNIRQRNVKGVNKIAKYRNVGSHAETSIVH

ELNHPATNEVISKMESASQPEHCDDWDNFTSGLEPY

TnsC (from *Aeromonas salmonicida* strain S44 plasmid pS44-1)

(SEQ ID NO: 5)
MDLSCHDADKLRSFIECYVETPLLRAIQEDFDRLRFNKQFAGEPQCMLL

TGDTGTGKSSLIRHYAAKHPEQVRHGFIHKPLLVSRIPSRPTLESTMVE

LLKDLGQFGSSDRIHKSSAESLTEALIKCLKRCETELIIIDEFQELIEN

KTREKRNQIANRLKYISETAKIPIVLVGMPWATKIAEEPQWSSRLLIRR

SIPYFKLSDDRENFIRLIMGLANRMPFETQARLETKHTIYALFAACYGS

LRALKQLLDESVKQALAAHAETLKHEHIAVAYALFYPDQVNPFLQPIDE

IKACEVKQYSRYEIDAAGKEEVLNPLQFTDKIPISQLLKKR

TnsC (E140A) change from *Aeromonas salmonicida* strain S44 plasmid pS44-1

(SEQ ID NO: 6)
MDLSCHDADKLRSFIECYVETPLLRAIQEDFDRLRFNKQFAGEPQCMLL

TGDTGTGKSSLIRHYAAKHPEQVRHGFIHKPLLVSRIPSRPTLESTMVE

LLKDLGQFGSSDRIHKSSAESLTEALIKCLKRCETELIIIDAFQELIEN

KTREKRNQIANRLKYISETAKIPIVLVGMPWATKIAEEPQWSSRLLIRR

SIPYFKLSDDRENFIRLIMGLANRMPFETQARLETKHTIYALFAACYGS

LRALKQLLDESVKQALAAHAETLKHEHIAVAYALFYPDQVNPFLQPIDE

IKACEVKQYSRYEIDAAGKEEVLNPLQFTDKIPISQLLKKR

TnsC (E140Q) change from *Aeromonas salmonicida* strain S44 plasmid pS44-1

(SEQ ID NO: 7)
MDLSCHDADKLRSFIECYVETPLLRAIQEDFDRLRFNKQFAGEPQCMLL

TGDTGTGKSSLIRHYAAKHPEQVRHGFIHKPLLVSRIPSRPTLESTMVE

LLKDLGQFGSSDRIHKSSAESLTEALIKCLKRCETELIIIDQFQELIEN

KTREKRNQIANRLKYISETAKIPIVLVGMPWATKIAEEPQWSSRLLIRR

SIPYFKLSDDRENFIRLIMGLANRMPFETQARLETKHTIYALFAACYGS

LRALKQLLDESVKQALAAHAETLKHEHIAVAYALFYPDQVNPFLQPIDE

IKACEVKQYSRYEIDAAGKEEVLNPLQFTDKIPISQLLKKR

Xre (gene 91099..91428, Locus tag CE463_00475) from *Aeromonas salmonicida* strain S44 plasmid pS44-1. The disclosure includes homologous Xre sequences. The sequence below is identical to the Xre protein in *Aeromonas hydrophila* strain AFG_SD03.

(SEQ ID NO: 8)
MTNPLPIRLKAARKATGLTQQQLGIRLGMEQSTASARMNQYEKGKHAPDY

QTMQRIAQELGYPVAYFYCDDELLAELICMMAKLSEEKQRELLQQLSVTE

YAESRDSAE

In addition to any of the foregoing mutations, the disclosure also includes additional amino acid changes, such as changes in TnsC, which may include gain-of-activity mutations, in canonical Tn7 (e.g., homologous proteins), including but not necessarily limited to TnsABC(A225V), TnsABC(E233K), TnsABC(E233A), and TnsABC(E233Q).

In one aspect the disclosure includes a kit comprising one or more expression vector(s) that encodes one or more Cas or other enzymes described herein. The expression vector in certain approaches includes a cloning site, such as a polycloning site, such that any desirable cargo gene(s) can be cloned into the cloning site to be expressed in any target cell into which the system is introduced or already comprises. The kit can further comprise one or more containers, printed material providing instructions as to how to use make and/or use the expression vector to produce suitable vectors, and reagents for introducing the expression vector into cells. The kits may further comprise one or more bacterial strains for use in producing the components of the system. The bacterial strains may be provided in a composition wherein growth of the bacteria is restricted, such as a frozen culture with one or more cryoprotectants, such as glycerol.

In another aspect the disclosure comprises delivering to cells a DNA cargo via a system of this disclosure. The method generally comprises introducing one or more polynucleotides of this disclosure, or a mixture or proteins and polynucleotides encoding the proteins, which may be also provided with RNA polynucleotides, into one or more bacterial or eukaryotic cells, whereby the Cas and transposon enzymes/proteins are expressed and editing of the chromosome or another DNA target by a combination of the Cas enzymes and the transposon occurs.

In non-limiting embodiments, this disclosure is considered to be suitable for targeting eukaryotic cells, and any microorganism that is susceptible to editing by a system as described herein. In embodiments the microorganism comprises bacteria that are resistant to one or more antibiotics, whereby the editing by the present system kills or reduces the growth of the antibiotic-resistant bacteria, and/or the system sensitizes the bacteria to an antibiotic by, for example, use of cargo that targets an antibiotic resistance gene, which may be present on a chromosome or a plasmid. The disclosure is thus suitable for targeting bacterial chromosomes or episomal elements, e.g., plasmids. In embodiments, a modification of a bacterial chromosome or plasmid causes the bacteria to change from pathogenic to non-pathogenic.

In embodiments, bacteria are killed. In embodiments, one or all of the components of a system described herein can be provided in a pharmaceutical formulation. Thus, in embodiments, DNA, RNA, proteins, and combinations thereof can be provided in a composition that comprises at least one pharmaceutically acceptable additive.

In embodiments, the method of this disclosure is used to reduce or eradicate bacterial cells, and may be used to reduce or eradicate persister bacteria and/or dormant viable but non-culturable (VBNC) bacteria from an individual or an inanimate surface, or a food substance.

In embodiments, and as noted above, the disclosure is considered suitable for editing eukaryotic cells. In embodiments, eukaryotic cells that are modified by the approaches of this disclosure are totipotent, pluripotent, multipotent, or oligopotent stem cells when the modification is made. In embodiments, the cells are neural stem cells. In embodiments, the cells are hematopoietic stem cells. In embodiments, the cells are leukocytes. In embodiments, the leukocytes are of a myeloid or lymphoid lineage. In embodiments, the cells are embryonic stem cells, or adult stem cells. In embodiments, the cells are epidermal stem cells or epithelial stem cells. In embodiments, the cells are cancer cells, or cancer stem cells. In embodiments, the cells are differentiated cells when the modification is made. In embodiments, the cells are mammalian cells. In embodiments, the cells are human, or are non-human animal cells. In embodiments, the non-human eukaryotic cells comprise fungal, plant or insect cells. In one approach the cells are engineered to express a detectable or selectable marker, or a combination thereof.

In embodiments, the disclosure includes obtaining cells from an individual, modifying the cells ex vivo using a CRISPR system as described herein, and reintroducing the cells or their progeny into the individual for prophylaxis and/or therapy of a condition, disease or disorder, or to treat an injury, trauma or anatomical defect. In embodiments, the cells modified ex vivo as described herein are used autologously.

In embodiments, cells modified according to this disclosure are provided as cell lines. In embodiments, the cells are engineered to produce a protein or other compound, and the cells themselves or the protein or compound they produce is used for prophylactic or therapeutic applications.

In various embodiments, the modification introduced into eukaryotic cells according to this disclosure is homozygous or heterozygous. In embodiments, the modification comprises a homozygous dominant or homozygous recessive or heterozygous dominant or heterozygous recessive mutation correlated with a phenotype or condition, and is thus useful for modeling such phenotype or condition. In embodiments a modification causes a malignant cell to revert to a non-malignant phenotype.

In certain aspects the disclosure includes a pharmaceutical formulation comprising one or more components of a system described herein. A pharmaceutical formulation comprises one or more pharmaceutically acceptable additives, many of which are known in the art. In some embodiments, the pharmaceutical compositions comprise a pharmaceutically acceptable carrier suitable for administration to humans. In some embodiments, the pharmaceutical compositions comprise a pharmaceutically acceptable carrier suitable for intraocular injection. In some embodiments, the pharmaceutical compositions comprise a pharmaceutically acceptable carrier suitable for topical application. In some embodiments, the pharmaceutical compositions comprise a pharmaceutically acceptable carrier suitable for intravenous injection. In some embodiments, the pharmaceutical compositions comprise and a pharmaceutically acceptable carrier suitable for injection into arteries. In some embodiments, the pharmaceutical composition is suitable for oral or topical administration. All of the described routes of administration are encompassed by the disclosure.

In embodiments, a system of this disclosure is administered to an individual in a therapeutically effective amount. The therapeutically effective amount, e.g., a dose, can be estimated initially either in cell culture assays or in animal models. An animal model can also be used to determine a suitable concentration range, and route of administration. Such information can then be used to determine useful doses and routes for administration in humans, or to non-human animals. A precise dosage can be selected by in view of the patient to be treated. Dosage and administration can be adjusted to provide sufficient levels of components to achieve a desired effect, such as a modification in a threshold number of cells. Additional factors which may be taken into account include the particular gene or other genetic element involved, the type of condition, the age, weight and gender of the patient, desired duration of treatment, method of administration, time and frequency of administration, drug combination(s), reaction sensitivities, and tolerance/response to therapy. In certain embodiments, a therapeutically effective amount is an amount that reduces one or more signs or symptoms of a disease, and/or reduces the severity of the disease. A therapeutically effective amount may also inhibit or prevent the onset of a disease, or a disease relapse. In embodiments, cells modified according to this disclosure are administered to an individual in need thereof in a therapeutically effective amount.

The following Examples are intended to illustrate but not limit the disclosure.

Example 1

This Example demonstrates increased transposition efficiency using a mutant TnsA protein as described herein, relative to a wild type TnsA protein, and thus demonstrates that TnsAs requires TnsA(A125D) for detectable RNA-guided transposition to native A.s. conjugal plasmid sequence in a heterologous host.

In particular, expression of TnsABC, TniQ, Cas8/5f, Cas6f, Cas7f, and native A.s. array in *E. coli* allows RNA-guided transposition to an *Aeromonas salmonicida* (A.s.)

conjugal plasmid sequence cloned onto F as monitored by a mate-out assay. Specifically, the following procedure was used.

BW27783 attTnT7::miniTn7(miniTn$^{A.s.}$-KanR)+F-native$^{A.s.}$+pBAD33-array$^{A.s.}$ strains were made chemically competent and double transformed with pBAD322-Gen TniQ/Cascade$^{A.s.}$ and pTA106, pTA106 TnsABC$^{A.s.}$ or pTA106 TnsABC$^{A.s.}$ (A125D) onto LB+100 µg/mL carbenicillin, 10 µg/mL gentamicin, 30 µg/mL chloramphenicol, 0.2% w/v glucose. After 24 hours incubation at 37° C., several hundred transformants were washed up in LB, diluted to a calculated OD of 0.02. 100 µL were plated on induction plates (LB+100 µg/mL carbenicillin, 10 µg/mL gentamicin, 30 µg/mL chloramphenicol, 0.2% w/v arabinose, 0.1 mM IPTG) and incubated for 16 hours at 37° C. Plates were washed up in LB, diluted to OD 6.86, and mixed 1:5 with OD 6.86 overnight culture of CW51. 20 µL drops were allowed to dry on LB plates and incubated for 4 hours at 37° C. Glass tubes were used to collect agar plugs with mated cells and 2 mLs LB were added and vortexed to extract cells from agar. Cells were serially diluted in LB+0.2% w/v glucose and plated on LB+20 µg/mL nalidixic acid, 100 µg/mL rifampicin, 100 µg/mL, spectinomycin with or without 50 µg/mL kanamycin to sample the entire transconjugant population or select for transposition respectively.

Transposition efficiency obtained from this approach are as follows:

TABLE 1

| Construct | Transposition efficiency |
| --- | --- |
| pTA106 (no transposon proteins, with guide RNA) | 0.0000% |
| pTA106 TnsABC-wt (full complement of proteins, with wild type TnsA, and guide RNA) | 0.0000% |
| pTA106 TnsABC-A125D (full complement of proteins, with TnsA A125D mutation and guide RNA) | 0.0188% |

Thus, the TnsA A125D change reverts a presumably inactivating mutation in the native element.

Experiments described in this Example are experimentally the same as in the following Example 2, except the TnsA A125D protein is used, along with the full complement of proteins and guide RNAs, which were targeted to lacZ-3 and lacZ-4, on opposite strands of the chromosome.

Example 2

This Example, following on the design of the analysis described in Example 1, demonstrates that mutant TnAs allows RNA-guided transposition from a chromosome to distinct F plasmid targets. Specifically, expression of TnsABC (TnsA A125D), TniQ, Cas8/5f, Cas6f, Cas7f, and single repeat-spacer-repeat array units in *E. coli* allows RNA-guided transposition to distinct F bound targets as monitored by a mate-out assay. Transposition was programmed with synthetic spacers to ffs$^{A.s.}$ with a perfect target match (ffs$^{exact}$) or with ten mismatches as found in the A.s. element (ffs$^{wild-type}$) or lacZ$^{E.c.}$ with two randomly selected TACC PAM protospacer sequences on either strand. Results are presented in FIG. 16. Sequences used to generate the data in this figure are as follows.

The segment of ffs gene from *Aeromonas salmonicida* S44 was included in the F plasmid as a target is as follows, where the protospacer is italicized and the PAM is in bold.

(SEQ ID NO: 9)
TCAGGACCGGAAGGTAGCAGCCAAGGCGGGGACTCGAGTGCCGGGATGT
GGCTGATGGGGCCACCAC

Guide RNA to ffs from *A. salmonicida* found in element CRISPR array (contains 10 mismatches.

(SEQ ID NO: 10)
AGGACUGGAAGAAAUCAUCCAAGUUGGGGACU

DNA equivalent as spacer 5'-AGGACTGGAAGAAATCATCCAAGTTGGGGACT-3') (SEQ ID NO:11)
Guide RNA to ffs from *A. salmonicida* but with 10 mismatches corrected (SEQ ID NO: 12)
AGGACCGGAAGGUAGCAGCCAAGGCGGGGAC (DNA equivalent as spacer 5'-AGGACCGGAAGGTAGCAGCCAAGGCGGGGAC-3' SEQ ID NO:13))

Sequence of the lacZ gene from *E. coli* that was included in the F plasmid as a target. Protospacer is italicized and the PAM sequences are in bold.

(SEQ ID NO: 14)
CCCAATACGCAAACCGCCTCTCCCCGCGCGTTGGCCGATTCATTAATGC
AGCTGGCACGACAGGTTTCCCGACTGGAAAGCGGGCAGTGAGCGCAACG
CAATTAATGTGAGTTAGCTCACTCATTAGGCACCCCAGGCTTTACACTT
TATGCTTCCGGCTCGTATGTTGTGTGGAATTGTGAGCGGATAACAATTT
CACACAGGAAACAGCTATGACCATGATTACGGATTCACTGGCCGTCGTT
TTACAACGTCGTGACTGGGAAAACCCTGGCGTTACCCAACTTAATCGCC
TTGCAGCACATCCCCCTTTCGCCAGCTGGCGTAATAGCGAAGAGGCCCG
CACCGATCGCCCTTCCCAACAGTTGCGCAGCCTGAATGGCGAATGGCGC
TTTGCCTGGTTTCCGGCACCAGAAGCGGTGCCGGAAAGCTGGCTGGAGT
GCGATCTTCCTGAGGCCGATACTGTCGTCGTCCCCTCAAACTGGCAGAT
GCACGGTTACGATGCGCCCATCTACACCAACGTGACCTATCCCATTACG
GTCAATCCGCCGTTTGTTCCCACGGAGAATCCGACGGGTTGTTACTCGC
TCACATTTAATGTTGATGAAAGCTGGCTACAGGAAGGCCAGACGCGAAT
TATTTTTGATGGCGTTAACTCGGCGTTTCATCTGTGGTGCAACGGGCGC
TGGGTCGGTTACGGCCAGGACAGTCGTTTGCCGTCTGAATTTGACCTGA
GCGCATTTTTACGCGCCGGAGAAAACCGCCTCGCGGTGATGGTGCTGCG
CTGGAGTGACGGCAGTTATCTGGAAGATCAGGATATGTGGCGGATGAGC
GGCATTTTCCGTGACGTCTCGTTGCTGCATAAACCGACTACACAAATCA
GCGATTTCCATGTTGCCACTCGCTTTAATGATGATTTCAGCCGCGCTGT
ACTGGAGGCTGAAGTTCAGATGTGCGGCGAGTTGCGTGACTACCTACGG
GTAACAGTTTCTTTATGGCAGGGTGAAACGCAGGTCGCCAGCGGCACCG

-continued

CGCCTTTCGGCGGTGAAATTATCGATGAGCGTGGTGGTTATGCCGATCG

CGTCACACTACGTCTGAACGTCGAAAACCCGAAACTGTGGAGCGCCGAA

ATCCCGAATCTCTATCGTGCGGTGGTTGAACTGCACACCGCCGACGGCA

CGCTGATTGAAGCAGAAGCCTGCGATGTCGGTTTCCGCGAGGTGCGGAT

TGAAAATGGTCTGCTGCTGCTGAACGGCAAGCCGTTGCTGATTCGAGGC

GTTAACCGTCACGAGCATCATCCTCTGCATGGTCAGGTCATGGATGAGC

AGACGATGGTGCAGGATATCCTGCTGATGAAGCAGAACAACTTTAACGC

CGT*GCGCTGTTCGCATTATCCGAACCATCCGCTGT*GGTACACGCTGTGC

GACCGCTACGGCCTGTATGTGGTGGATGAAGCCAATATTGAAACCCACG

GCATGGTGCCAATGAATCGTCTGACCGATGATCCGCGCTGGCTACCGGC

GATGAGCGAACGCGTAACGCGAATGGTGCAGCGCGATCGTAATCACCCG

AGTGTGATCATCTGGTCGCTGGGGAATGAATCAGGCCACGGCGCTAATC

ACGACGCGCTGTATCGCTGGATCAAATCTGTCGATCCTTCCCGCCCGGT

GCAGTATGAAGGCGGCGGAGCCGACACCACGGCCACCGATATTATTTGC

CCGATGTACGCGCGCGTGGATGAAGACCAGCCCTTCCCGGCTGTGCCGA

AATGGTCCATCAAAAAATGGCTTTCGCTACCTGGAGAGACGCGCCCGCT

GATCCTTTGCGAATACGCCCACGCGATGGGTAACAGTCTTGGCGGTTTC

GCTAAATACTGGCAGGCGTTTCGTCAGTATCCCCGTTTACAGGGCGGCT

TCGTCTGGGACTGGGTGGATCAGTCGCTGATTAAATATGATGAAAACGG

CAACCCGTGGTCGGCTTACGGCGGTGATTTTGGCGATACGCCGAACGAT

CGCCAGTTCTGTATGAACGGTCTGGTCTTTGCCGACCGCACGCCGCATC

CAGCGCTGACGGAAGCAAAACACCAGCAGCAGTTTTTCCAGTTCCGTTT

ATCCGGGCAAACCATCGAAGTGACCAGCGAATACCTGTTCCGTCATAGC

GATAACGAGCTCCTGCACTGGATGGTGGCGCTGGATGGTAAGCCGCTGG

CAAGCGGTGAAGTGCCTCTGGATGTCGCTCCACAAGGTAAACAGTTGAT

TGAACTGCCTGAACTACCGCAGCCGGAGAGCGCCGGGCAACTCTGGCTC

ACAGTACGCGTAGTGCAACCGAACGCGACCGCATGGTCAGAAGCCGGGC

ACATCAGCGCCTGGCAGCAGTGGCGTCTGGCGGAAAACCTCAGTGTGAC

GCTCCCCGCCGCGTCCCACGCCATCCCGCATCTGACCCACCAGCGAAATG

GATTTTTGCATCGAGCTGGGTAATAAGCGTTGGCAATTTAACCGCCAGT

CAGGCTTTCTTTCACAGATGTGGATTGGCGATAAAAAACAACTGCTGAC

GCCGCTGCGCGATCAGTTCACCCGTGCACCGCTGGATAACGACATTGGC

GTAAGTGAAGCGACCCGCATTGACCCTAACGCCTGGGTCGAACGCTGGA

AGGCGGCGGGCCATTACCAGGCCGAAGCAGCGTTGTTGCAGTGCACGGC

AGATACACTTGCTGATGCGGTGCTGATTACGACCGCTCACGCGTGGCAG

CATCAGGGGAAAACCTTATTTATCAGCCGGAAAACCTACCGGATTGATG

GTAGTGGTCAAATGGCGATTACCGTTGATGTTGAAGTGGCGAGCGATAC

ACCGCATCCGGCGCGGATTGGCCTGAACTGCCAGCTGGCGCAGGTAGCA

GAGCGGGTAAACTGGCTCGGATTAGGGCCGCAAGAAAACTATCCCGACC

GCCTTACTGCCGCCTGTTTTGACCGCTGGGATCTGCCATTGTCAGACAT

GTATACCCCGTACGTCTTCCCGAGCGAAAACGGTCTGCGCTGCGGGACG

-continued

CGCGAATTGAATTATGGCCCACACCAGTGGCGCGGCGACTTCCAGTTCA

ACATCAGCCGCTACAGTCAACAGCAACTGATGGAAACCAGCCATCGCCA

TCTGCTGCACGCGGAAGAAGGCACATGGCTGAATATCGACGGTTTCCAT

ATGGGGATTGGTGGCGACGACTCCTGGAGCCCGTCAGTATCGGCGGAAT

TCCAGCTGAGCGCCGGTCGCTACCATTACCAGTTGGTCTGGTGTCAAAA

ATAATAATAACCGGGCAGGCCATGTCTCTTGCGCTCGTTCGCCAGCCAG

GACAGAAATGCCTCGACTTCGCTGCTGCCCAAGGTTGCCGGGTGACGCA

CACCGTGGAAACGGATGAAGGCACGAACCCAGTGGACATAAGCCTGTTC

GGTTCGTAAGCTGTAATGCAAGTAGCGTATGCGCTCACGCAACTGGTCC

AGAACCTTGACCGAACGCAGCGGTGGTAACGGCGCAGTGGCGGTTTTCA

TGGCTTGTTATGACTGTTTTTTTGGGGTACAGTCTATGCCTCGGGCATC

CAAGCAGCAAGCGCGTTACGCCGTGGGTCGATGTTTGATGTTATGGAGC

AGCAACGATGTTACGCAGCAGGGCAGTCGCCCTAAAACAAAGTTAAACA

TCATGAGGGAAGCGGTGATCGCCGAAGTATCGACTCAACTATCAGAGGT

AGTTGGCGTCATCGAGCGCCATCTCGAACCGACGTTGCTGGCCGTACAT

TTGTACGGCTCCGCAGTGGATGCGGCCTGAAGCCACACAGTGATATTG

ATTTGCTGGTTACGGTGACCGTAAGGCTTGATGAAACAACGCGGCGAGC

TTTGATCAACGACCTTTTGGAAACTTCGGCTTCCCCTGGAGAGAGCGAG

ATTCTCCGCGCTGTAGAAGTCACCATTGTTGTGCACGACGACATCATTC

CGTGGCGTTATCCAGCTAAGCGCGAACTGCAATTTGGAGAATGGCAGCG

CAATGACATTCTTGCAGGTATCTTCGAGCCAGCCACGATCGACATTGAT

CTGGCTATCTTGCTGACAAAAGCAAGAGAACATAGCGTTGCCTTGGTAG

GTCCAGCGGCGGAGGAACTCTTTGATCCGGTTCCTGAACAGGATCTATT

TGAGGCGCTAAATGAAACCTTAACGCTATGGAACTCGCCGCCCGACTGG

GCTGGCGATGAGCGAAATGTAGTGCTTACGTTGTCCCGCATTTGGTACA

GCGCAGTAACCGGCAAAATCGCGCCGAAGGATGTCGCTGCCGACTGGGC

AATGGAGCGCCTGCCGGCCCAGTATCAGCCCGTCATACTTGAAGCTAGA

CAGGCTTATCTTGGACAAGAAGAAGATCGCTTGGCCTCGCGCGCAGATC

AGTTGGAAGAATTTGTCCACTACGTGAAAGGCGAGATCACCAAGGTAGT

CGGCAAATAATGTCTAACAATTCGTTCAAGCCGACGCCGCTTCGCGGCG

CGGCTTAACTCAA

Guide RNA lacZ3, perfect match (SEQ ID NO: 15)

UACGGGUAACAGUUUCUUUAUGGCAGGGUGAA (DNA equivalent as spacer 5'-TACGGGTAACAGTTTCTTTA

TGGCAGGGTGAA-3' (SEQ ID NO: 16))

Guide RNA lacZ4, perfect match (SEQ ID NO: 17)

ACAGCGGAUGGUUCGGAUAAUGCGAACAGCGC (DNA equivalent as spacer 5'-ACAGCGGATGGTTCGGATAA

TGCGAACAGCGC (SEQ ID NO: 18)

Figure 16:
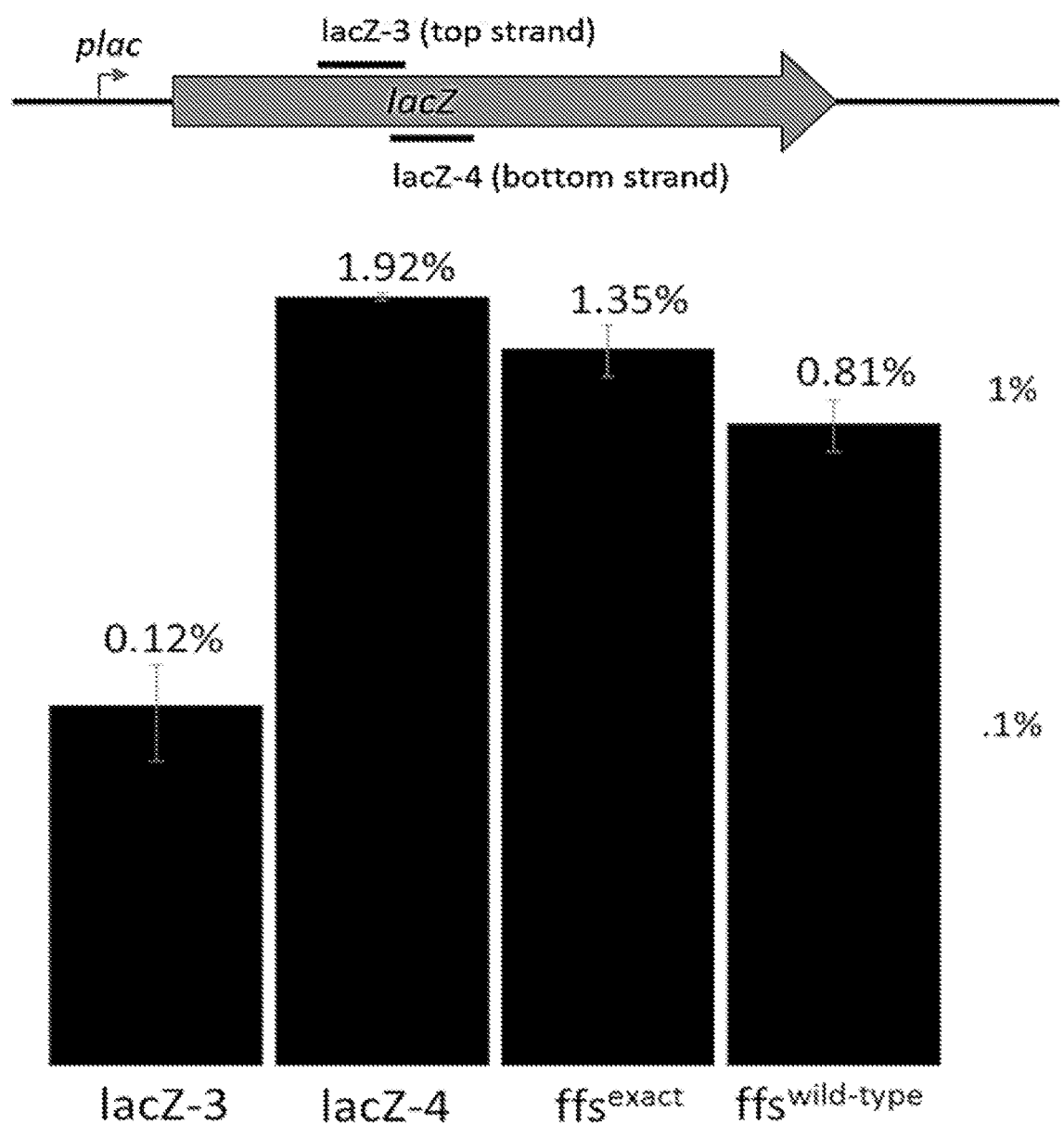
FIG. 16. Graphical data obtained with the mate-out assay depicted in FIGS. 13 and 14. The results demonstrate that transposon insertions can be programed to insert into either a lacZ targeted (depicted in the cartoon) or a portion of the native ffs gene native target found in *A. salmonicida* (not cartooned). All of the protospacer targets have the TACC PAM. Targets were selected for the lacZ gene as specific for the top or bottom strand and the relative position indicated (it is unclear why an ~10-fold difference in frequency is found with different protospacers). The native ffs guide RNA (ffswild-type) has 10 mismatches to the native ffs gene. Making the guide RNA a perfect match (ffsexact) increases the frequency of transposition.
Figure 17:
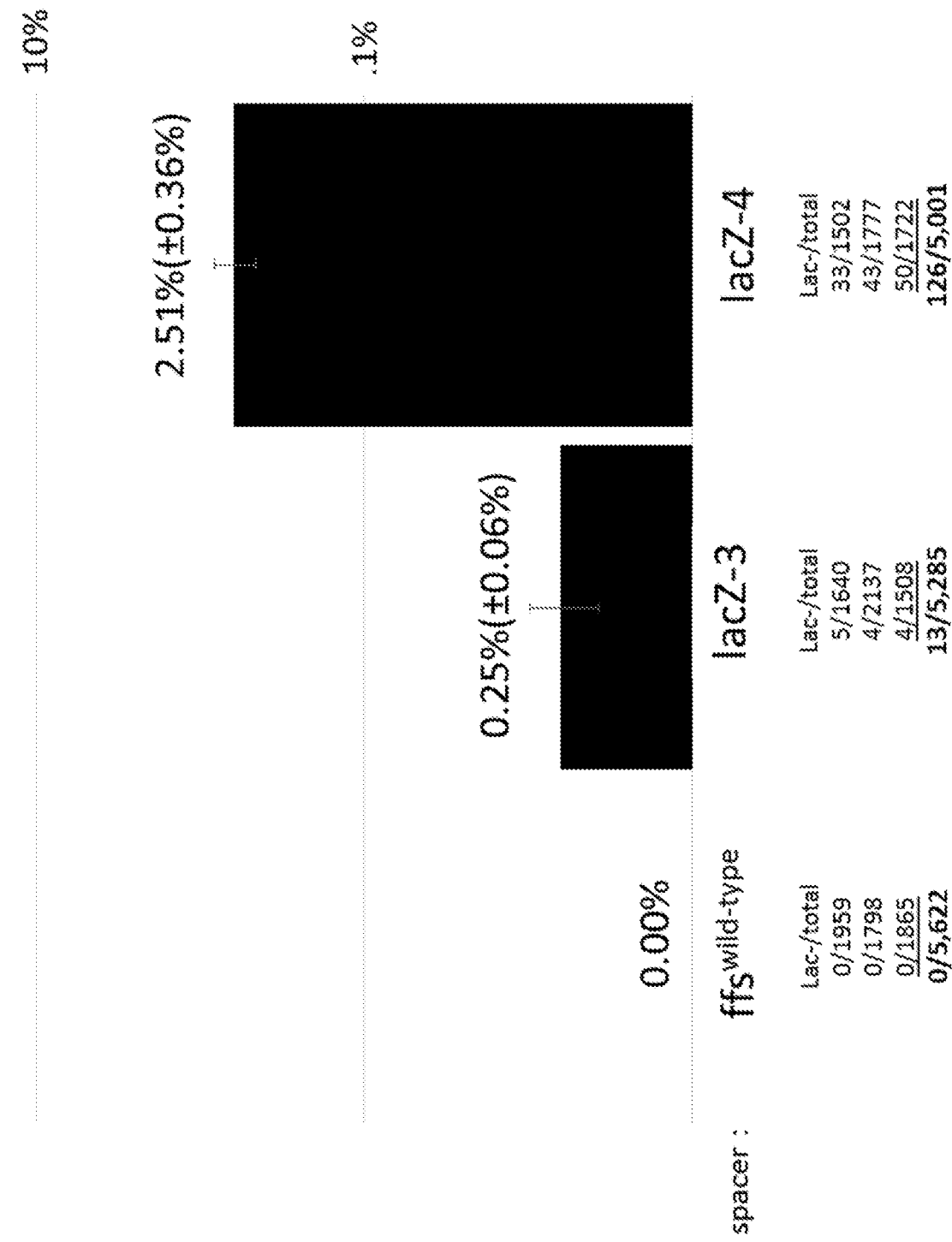
FIG. 17. Graphical data demonstrating that TnsA allows RNA-guided transposition to chromosomal lacZ. Expression of TnsABC (TnsA A125D), TniQ, Cas8/5f, Cas6f, Cas7f, and single repeat-spacer-repeat array units in *E. coli* allows RNA-guided transposition to lacZ as monitored by Lac phenotype on MacConkey agar. Transposition can be programmed with synthetic spacers to lacZ with two randomly selected TACC PAM protospacer sequences on either strand (the same lacZ specific guider RNAs used in FIG. 19). The actual data used to calculate the percentages shown in the graph from the three replicates is indicate below the graph.

To obtain the results shown in FIG. 16, the following procedures were used with the above described spacers and guide RNAs.

BW27783 attTn7::miniTn7(miniTn$^{A.s.}$-KanR)+F-(target) strains were made Inoue competent and triple transformed with pTA106 TnsABC$^{A.s.}$(A125D), pBAD322-Gen TniQ/Cascade$^{A.s.}$, and pBAD33-single array units with various guides onto LB+100 µg/mL carbenicillin, 10 µg/mL gentamicin, 30 µg/mL chloramphenicol, 0.2% w/v glucose. After 16 hours incubation at 37° C., several hundred transformants were washed up in M9 maltose. 100 µL washed up transformant pools were added to 3 mL liquid induction media (LB+100 µg/mL carbenicillin, 10 µg/mL gentamicin, 30 µg/mL chloramphenicol, 0.2% w/v arabinose, 0.1 mM IPTG) and incubated shaking for 24 hours at 30° C. 250 µL induced cultures were washed once in LB+0.2% w/v glucose and resuspended in 1 mL LB+0.2% w/v glucose. 500 µL were transferred to a glass tube and incubated shaking for 2 hours at 37° C. to allow recovery from minimal media and expression of conjugation machinery. After incubation 5 mLs mid-log CW51 (overnight culture CW51 subcultured 1:50 into LB+0.2% w/v glucose and grown for 2.5 hours) were added to each tube and incubated with gentle shaking at 37° C. to allow plasmid transfer. After 1.5 hours, cultures were vortexed to disrupt mating pairs, placed on ice, then serially diluted in LB+0.2% w/v glucose and plated on LB+20 µg/mL nalidixic acid, 100 µg/mL rifampicin, 100 µg/mL spectinomycin, 50 µg/mL X-gal, with or without 50 µg/mL kanamycin to sample the entire transconjugant population or select for transposition respectively.

Example 3

This Example provides results demonstrating that Tn$^{A.s.}$ allows RNA-guided transposition in cis to chromosomal lacZ.

In more detail, this Example uses the same transposon and Cas proteins described above, but demonstrates intra-chromosomal transposition using different targeted and control guide RNAs. In particular, the control guide RNA is directed to the ffs target used above, but the guide RNAs in this Example are programmed for guide-RNA directed editing such that they target the LacZ gene only. Results are shown in FIG. 17. In particular, the results demonstrate that expression of TnsABC (TnsA A125D), TniQ, Cas8/5f, Cas6f, Cas7f, and single repeat-spacer-repeat array units in E. coli allows RNA-guided transposition to lacZ as monitored by Lac phenotype on MacConkey agar. Transposition can thus be programmed with synthetic spacers to lacZ with two randomly selected TACC PAM protospacer sequences on either strand. To obtain the results described in this Example, the following materials and methods were used.

Figure 18:
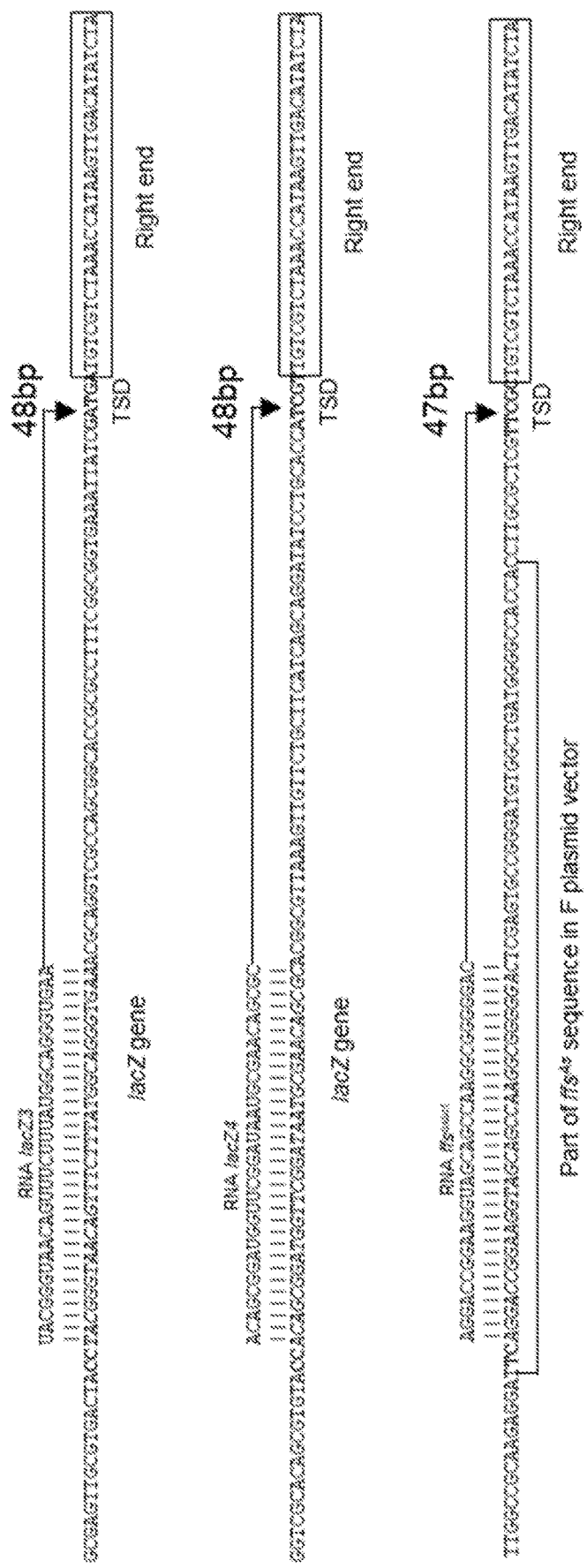
FIG. 18. Depiction of relationship between spacer and protospacer with the gene targeted and the position of the insertion. Five different genes targeted by guide RNAs are indicated by the spacers found in the array. Matches between the guide RNA and protospacer are indicated by a short vertical line. The five base-pair target site duplication (TSD) is indicated along with the distance from the protospacer recognized by the guide RNA to. The right end of the transposon is indicated. The RNA lacZ3 is SEQ ID NO:15, The RNA lacZ4 is SEQ ID NO:17. The RNA RNA ffs$^{exact}$ is SEQ ID NO: 12. The uppermost DNA strand is SEQ ID NO:19. The middle DNA strand is SEQ ID NO:20. The bottom DNA strand is SEQ ID NO:21.

BW27783 Lac+attTn7::miniTn7(miniTnAs-KanR) was made calcium competent and triple transformed with pTA106 TnsABC$^{As}$(A125D), pBAD322-Gen TniQ/Cascade$^{As}$, and pBAD33-single array units with various guides onto LB+100 µg/mL carbenicillin, 10 µg/ml gentamicin 30 µg/mL chloramphenicol, 0.2% w/v glucose. After 16 hours incubation at 37° C., several hundred transformants were washed up in M9 maltose. Cells were diluted in 3 mL liquid induction media (LB+100 µg/mL carbenicillin, 10 µg/mL gentamicin, 30 µg/L chloramphenicol, 0.2% w/v arabinose, 0.1 mM IPTG) to a calculated OD 0.2. After 24 hour incubation at 30° C., cells were diluted and plated on Mac Lac. After 16 hours incubation at 37° C., white and red colonies were counted. Insertions directed into the lacZ are indicated with a color change on indicator media, wherein a Lac- colony is white and a Lac+ is red on MacConkey's media. The pBAD33-single array units encoding lacZ3, lacZ4, and ffs$^{wild-type}$ guide RNAs were the same as used in Example 2. The E. coli native lacZ gene targeted in these is shown in Example 2. There was no match to the ffs$^{wild-type}$ guide RNAs so that it could act as a negative control. FIG. 18 depicts pertinent segments of the guide RNAs for each gene, and the target sequences in relation to the TSD and the right end.

While the disclosure has been particularly shown and described with reference to specific embodiments, it should be understood by those having skill in the art that various changes in form and detail may be made therein without departing from the spirit and scope of the present disclosure as disclosed herein.

What is claimed is:

1. A method for modifying a chromosome or extrachromosomal element in one or more prokaryotic cells, the method comprising introducing into the one or more prokaryotic cells a TnsA transposon protein that is at least 90% similar to SEQ ID NO:1 but contains an amino acid other than Alanine at position 125 of SEQ ID NO:1; or an expression vector comprising a tnsA gene that encodes and expresses said TnsA transposon protein when introduced into the one or more prokaryotic cells;
wherein the one or more prokaryotic cells also comprise during said modifying:
transposon proteins TnsB, TnsC, TniQ,
Cas proteins Cas8f, Cas5f, Cas7f, Cas6f,
a transposable DNA cargo sequence that is flanked by left and right transposon sequences; and
at least one guide RNA comprising a spacer targeted to a target DNA sequence in the chromosome or the extrachromosomal element, the DNA target sequence comprising a protospacer and a protospacer adjacent motif (PAM) that is 5' to the protospacer;
wherein the TnsA, TnsB, TnsC, TniQ, Cas8f, Cas5f, Cas7f, Cas6f, and the at least one guide RNA, participate in transposition of the transposable DNA cargo sequence into the chromosome or extrachromosomal element in a location that is 3' relative to the PAM and the protospacer.

2. The method of claim 1, wherein the TnsA transposon protein is at least 90% similar to SEQ ID NO:1 and comprises a D at position 125 of SEQ ID NO:1.

3. The method of claim 2, wherein the TnsA transposon protein comprises SEQ ID NO:2.

4. The method of claim 1, wherein efficiency of transposition of the transposable DNA cargo in a population of prokaryotic cells is more efficient than transposition obtained from a control using a TnsA transposon protein that comprises an amino acid sequence that is at least 90% similar to SEQ ID NO:1 and contains an Alanine at position 125.

5. The method of claim 4, wherein at least one of the TnsA, TnsB, TnsC, TniQ, Cas8f, Cas5f, Cas7f, and Cas6f proteins is expressed in the one or more prokaryotic cells from an expression vector.

6. The method of claim 5, wherein the TnsA protein is expressed from an expression vector, and wherein at least one of TnsB, TnsC, TniQ, Cas8f, Cas5f, Cas7f, Cas6f, is also expressed from the same expression vector.

7. The method of claim 6, wherein the TnsA, TnsB, TnsC, TniQ, Cas8f, Cas5f, Cas7f, Cas6f, are all expressed from the same expression vector.

8. The method of claim 5, wherein the at least one guide RNA is introduced into the one or more prokaryotic cells as an RNA polynucleotide.

9. The method of claim 5, wherein the at least one guide RNA is expressed from an expression vector within the one or more prokaryotic cells.

10. The method of claim 9, wherein the expression vector that expresses the guide RNA also comprises the transposable DNA cargo.

11. The method of claim 9, wherein the expression vector that expresses the at least one guide RNA is distinct from an expression vector that expresses at least one of the TnsA, TnsB, TnsC, TniQ, Cas8f, Cas5f, Cas7f, and Cas6 proteins.

12. The method of claim 10, wherein the expression vector that expresses the at least one guide RNA is distinct from an expression vector that expresses at least one of the TnsA, TnsB, TnsC, TniQ, Cas8f, Cas5f, Cas7f, and Cas6 proteins.

13. The method of claim 1, wherein the TnsA, TnsB, TnsC, TniQ, cas8f, cas5f, cas7f, and cas6f proteins are expressed within the one or more prokaryotic cells from the same expression vector, wherein the at least one guide RNA is expressed from an expression vector within the one or more prokaryotic cells that is distinct from the expression vector that expresses the TnsA, TnsB, TnsC, TniQ, cas8f, cas5f, cas7f and cas6f proteins, wherein the expression vector that expresses the guide RNA also comprises the transposable DNA cargo, and wherein TnsA protein comprises the sequence of SEQ ID NO:2.

14. The method of claim 13, wherein the transposable DNA cargo sequence is transposed into the chromosome or extrachromosomal element wherein the transposable DNA cargo sequence is transposed into the chromosome or extrachromosomal element within 42-52 nucleotides 3' relative to the 3' end of the protospacer.

* * * * *

SEQUENCE LISTING

<160> NUMBER OF SEQ ID NOS: 21

<210> SEQ ID NO 1
<211> LENGTH: 215
<212> TYPE: PRT
<213> ORGANISM: artificial sequence
<220> FEATURE:
<223> OTHER INFORMATION: Modified Aeromonas salmonicida TnsA protein

<400> SEQUENCE: 1

Met Tyr Arg Arg His Leu Lys His Ser Arg Val Lys Asn Leu Phe Lys
1               5                   10                  15

Phe Val Ser Ala Lys Met Asn Thr Val Phe Thr Val Glu Ser Ala Leu
            20                  25                  30

Glu Phe Asp Thr Cys Phe His Leu Glu Tyr Ser Pro Ser Val Lys Phe
        35                  40                  45

Tyr Glu Ala Gln Pro Glu Gly Phe Tyr Tyr Glu Phe Ala Gly Arg Gln
    50                  55                  60

Cys Pro Tyr Thr Pro Asp Phe Arg Leu Val Asp Gln Asn Asp Ser Val
65                  70                  75                  80

Ser Phe Leu Glu Ile Lys Pro Ser Asp Lys Val Ala Asp Pro Asp Phe

```
                85                  90                  95
Leu His Arg Phe Pro Leu Lys Gln Gln Arg Ala Ile Glu Leu Ser Ser
            100                 105                 110
Pro Leu Lys Leu Val Thr Glu Lys Gln Ile Arg Ile Asp Pro Ile Leu
        115                 120                 125
Gly Asn Leu Lys Leu Leu His Arg Tyr Ser Gly Phe Gln Ser Phe Thr
    130                 135                 140
Pro Leu His Met Gln Leu Leu Gly Leu Val Gln Lys Leu Gly Arg Val
145                 150                 155                 160
Ser Leu Leu Arg Leu Ser Asp Ser Ile Asp Ala Pro Pro Glu Glu Val
                165                 170                 175
Leu Ala Ser Ala Leu Ser Leu Ile Ala Arg Gly Ile Met Gln Ser Asp
            180                 185                 190
Leu Thr Val Gln Lys Ile Gly Ile Ser Ser Phe Val Trp Ala Gly Gly
        195                 200                 205
His Ser Gly Ile Asp His Gly
    210                 215

<210> SEQ ID NO 2
<211> LENGTH: 215
<212> TYPE: PRT
<213> ORGANISM: Aeromonas salmonicida

<400> SEQUENCE: 2

Met Tyr Arg Arg His Leu Lys His Ser Arg Val Lys Asn Leu Phe Lys
1               5                   10                  15
Phe Val Ser Ala Lys Met Asn Thr Val Phe Thr Val Glu Ser Ala Leu
            20                  25                  30
Glu Phe Asp Thr Cys Phe His Leu Glu Tyr Ser Pro Ser Val Lys Phe
        35                  40                  45
Tyr Glu Ala Gln Pro Glu Gly Phe Tyr Tyr Gly Phe Ala Gly Arg Gln
    50                  55                  60
Cys Pro Tyr Thr Pro Asp Phe Arg Leu Val Asp Gln Asn Asp Ser Val
65                  70                  75                  80
Ser Phe Leu Glu Ile Lys Pro Ser Asp Lys Val Ala Asp Pro Asp Phe
                85                  90                  95
Leu His Arg Phe Pro Leu Lys Gln Gln Arg Ala Ile Glu Leu Ser Ser
            100                 105                 110
Pro Leu Lys Leu Val Thr Glu Lys Gln Ile Arg Ile Ala Pro Ile Leu
        115                 120                 125
Gly Asn Leu Lys Leu Leu His Arg Tyr Ser Gly Phe Gln Ser Phe Thr
    130                 135                 140
Pro Leu His Met Gln Leu Leu Gly Leu Val Gln Lys Leu Gly Arg Val
145                 150                 155                 160
Ser Leu Leu Arg Leu Ser Asp Ser Ile Asp Ala Pro Pro Glu Glu Val
                165                 170                 175
Leu Ala Ser Ala Leu Ser Leu Ile Ala Arg Gly Ile Met Gln Ser Asp
            180                 185                 190
Leu Thr Val Gln Lys Ile Gly Ile Ser Ser Phe Val Trp Ala Gly Gly
        195                 200                 205
His Ser Gly Ile Asp His Gly
    210                 215

<210> SEQ ID NO 3
<211> LENGTH: 624
```

```
<212> TYPE: PRT
<213> ORGANISM: Aeromonas salmonicida

<400> SEQUENCE: 3
```

Met Asp Lys His Asn Gly Gly Leu Phe Glu Asp Glu Phe Val Ile Pro
1               5                   10                  15

Gln Pro Ser Thr Ser Thr Ser Pro Ile Asp Ala Ile Gln Ala Val Leu
            20                  25                  30

Pro Ala Thr Val Asp Ser Phe Pro Tyr Val Leu Lys Val Glu Ala Leu
            35                  40                  45

His Arg Arg Asp Tyr Ile Leu Trp Val Glu Lys Asn Leu Ala Gly Gly
        50                  55                  60

Trp Thr Glu Lys Asn Leu Thr Pro Leu Leu Ala Asp Ala Ala Leu Val
65                  70                  75                  80

Leu Pro Pro Pro Thr Pro Asn Trp Arg Thr Leu Ala Arg Trp Arg Lys
                85                  90                  95

Ile Tyr Ile Gln His Gly Arg Lys Leu Val Ser Leu Ile Pro Lys His
            100                 105                 110

Gln Ala Lys Gly Asn Ala Arg Ser Arg Leu Pro Pro Ser Asp Glu Leu
            115                 120                 125

Phe Phe Glu Gln Ala Val His Arg Tyr Leu Val Gly Glu Gln Pro Ser
130                 135                 140

Ile Ala Ser Ala Phe Gln Leu Tyr Ser Asp Ser Ile Arg Ile Glu Asn
145                 150                 155                 160

Leu Gly Val Val Glu Asn Pro Ile Lys Thr Ile Ser Tyr Met Ala Phe
                165                 170                 175

Tyr Asn Arg Ile Lys Lys Leu Pro Ala Tyr Gln Val Met Lys Ser Arg
            180                 185                 190

Lys Gly Ser Tyr Ile Ala Asp Val Glu Phe Lys Ala Ile Ala Ser His
            195                 200                 205

Lys Pro Pro Ser Arg Ile Met Glu Arg Val Gly Ile Asp His Thr Pro
210                 215                 220

Leu Asp Leu Leu Leu Leu Asp Asp Leu Leu Val Pro Leu Gly Arg
225                 230                 235                 240

Pro Ser Leu Thr Leu Leu Ile Asp Ala Tyr Ser His Cys Val Val Gly
            245                 250                 255

Phe Asn Leu Asn Phe Asn Gln Pro Ser Tyr Glu Ser Val Arg Asn Ala
            260                 265                 270

Leu Leu Ser Ser Ile Ser Lys Lys Asp Tyr Val Lys Asn Lys Tyr Pro
            275                 280                 285

Ser Ile Glu His Glu Trp Pro Cys Tyr Gly Lys Pro Glu Thr Leu Val
            290                 295                 300

Val Asp Asn Gly Val Glu Phe Trp Ser Ala Ser Leu Ala Gln Ser Cys
305                 310                 315                 320

Leu Glu Leu Gly Ile Asn Ile Gln Tyr Asn Pro Val Arg Lys Pro Trp
                325                 330                 335

Leu Lys Pro Met Ile Glu Arg Met Phe Gly Ile Ile Asn Arg Lys Leu
            340                 345                 350

Leu Glu Pro Ile Pro Gly Lys Thr Phe Ser Asn Ile Gln Glu Lys Gly
            355                 360                 365

Asp Tyr Asp Pro Gln Lys Asp Ala Val Met Arg Phe Ser Thr Phe Leu
            370                 375                 380

Glu Ile Phe His His Trp Val Ile Asp Val Tyr His Tyr Glu Pro Asp
385                 390                 395                 400

```
Ser Arg Tyr Arg Tyr Ile Pro Ile Ile Ser Trp Gln His Gly Asn Lys
            405                 410                 415

Asp Ala Pro Pro Ala Pro Ile Ile Gly Asp Asp Leu Thr Lys Leu Glu
        420                 425                 430

Val Ile Leu Ser Leu Ser Leu His Cys Thr His Arg Arg Gly Gly Ile
            435                 440                 445

Gln Arg Tyr His Leu Arg Tyr Asp Ser Asp Glu Leu Ala Ser Tyr Arg
        450                 455                 460

Met Asn Tyr Pro Asp Gln Thr Arg Gly Lys Arg Lys Val Leu Val Lys
465                 470                 475                 480

Leu Asn Pro Arg Asp Ile Ser Tyr Val Tyr Val Phe Leu Glu Asp Leu
            485                 490                 495

Gly Ser Tyr Ile Arg Val Pro Cys Ile Asp Pro Ile Gly Tyr Thr Lys
            500                 505                 510

Gly Leu Ser Leu Gln Glu His Gln Ile Asn Val Lys Leu His Arg Asp
        515                 520                 525

Phe Ile Asn Glu Gln Met Asp Val Val Ser Leu Ser Lys Ala Arg Ile
        530                 535                 540

Tyr Leu Asn Asp Arg Ile Lys Asn Glu Leu Ile Glu Val Arg Arg Asn
545                 550                 555                 560

Ile Arg Gln Arg Asn Val Lys Gly Val Asn Lys Ile Ala Lys Tyr Arg
                565                 570                 575

Asn Val Gly Ser His Ala Glu Thr Ser Ile Val His Glu Leu Asn His
            580                 585                 590

Pro Ala Thr Asn Glu Val Ile Ser Lys Met Glu Ser Ala Ser Gln Pro
        595                 600                 605

Glu His Cys Asp Asp Trp Asp Asn Phe Thr Ser Gly Leu Glu Pro Tyr
    610                 615                 620

<210> SEQ ID NO 4
<211> LENGTH: 624
<212> TYPE: PRT
<213> ORGANISM: artificial sequence
<220> FEATURE:
<223> OTHER INFORMATION: modification of AS TnsB

<400> SEQUENCE: 4

Met Asp Lys His Asn Gly Gly Leu Phe Glu Asp Glu Phe Val Ile Pro
1               5                   10                  15

Gln Pro Ser Thr Ser Thr Ser Pro Ile Asp Ala Ile Gln Ala Val Leu
            20                  25                  30

Pro Ala Thr Val Asp Ser Phe Pro Tyr Val Leu Lys Val Glu Ala Leu
        35                  40                  45

His Arg Arg Asp Tyr Ile Leu Trp Val Glu Lys Asn Leu Ala Gly Gly
    50                  55                  60

Trp Thr Glu Lys Asn Leu Thr Pro Leu Leu Ala Asp Ala Ala Leu Val
65              70                  75                  80

Leu Pro Pro Thr Pro Asn Trp Arg Thr Leu Ala Arg Trp Arg Lys
            85                  90                  95

Ile Tyr Ile Gln His Gly Arg Lys Leu Val Ser Leu Ile Pro Lys His
            100                 105                 110

Gln Ala Lys Gly Asn Ala Arg Ser Arg Leu Pro Pro Ser Asp Glu Leu
        115                 120                 125

Phe Phe Glu Gln Ala Val His Arg Tyr Leu Val Gly Glu Gln Pro Ser
    130                 135                 140
```

```
Ile Ala Ser Ala Phe Gln Leu Tyr Ser Asp Ser Ile Arg Ile Glu Asn
145                 150                 155                 160

Leu Gly Val Val Glu Asn Ser Ile Lys Thr Ile Ser Tyr Met Ala Phe
            165                 170                 175

Tyr Asn Arg Ile Lys Lys Leu Pro Ala Tyr Gln Val Met Lys Ser Arg
        180                 185                 190

Lys Gly Ser Tyr Ile Ala Asp Val Glu Phe Lys Ala Ile Ala Ser His
    195                 200                 205

Lys Pro Pro Ser Arg Ile Met Glu Arg Val Glu Ile Asp His Thr Pro
210                 215                 220

Leu Asp Leu Leu Leu Asp Asp Leu Leu Val Pro Leu Gly Arg
225                 230                 235                 240

Pro Ser Leu Thr Leu Leu Ile Asp Ala Tyr Ser His Cys Val Val Gly
            245                 250                 255

Phe Asn Leu Asn Phe Asn Gln Pro Ser Tyr Glu Ser Val Arg Asn Ala
        260                 265                 270

Leu Leu Ser Ser Ile Ser Lys Lys Asp Tyr Val Lys Asn Lys Tyr Pro
    275                 280                 285

Ser Ile Glu His Glu Trp Pro Cys Tyr Gly Lys Pro Glu Thr Leu Val
290                 295                 300

Val Asp Asn Gly Val Glu Phe Trp Ser Ala Ser Leu Ala Gln Ser Cys
305                 310                 315                 320

Leu Glu Leu Gly Ile Asn Ile Gln Tyr Asn Pro Val Arg Lys Pro Trp
            325                 330                 335

Leu Lys Pro Met Ile Glu Arg Met Phe Gly Ile Ile Asn Arg Lys Leu
        340                 345                 350

Leu Glu Pro Ile Pro Gly Lys Thr Phe Ser Asn Ile Gln Glu Lys Gly
    355                 360                 365

Asp Tyr Asp Pro Gln Lys Asp Ala Val Met Arg Phe Ser Thr Phe Leu
370                 375                 380

Glu Ile Phe His His Trp Val Ile Asp Val Tyr His Tyr Glu Pro Asp
385                 390                 395                 400

Ser Arg Tyr Arg Tyr Ile Pro Ile Ile Ser Trp Gln His Gly Asn Lys
            405                 410                 415

Asp Ala Pro Pro Ala Pro Ile Ile Gly Asp Asp Leu Thr Lys Leu Glu
        420                 425                 430

Val Ile Leu Ser Leu Ser Leu His Cys Thr His Arg Arg Gly Gly Ile
    435                 440                 445

Gln Arg Tyr His Leu Arg Tyr Asp Ser Asp Glu Leu Ala Ser Tyr Arg
450                 455                 460

Met Asn Tyr Pro Asp Gln Thr Arg Gly Lys Arg Lys Val Leu Val Lys
465                 470                 475                 480

Leu Asn Pro Arg Asp Ile Ser Tyr Val Tyr Val Phe Leu Glu Asp Leu
            485                 490                 495

Gly Ser Tyr Ile Arg Val Pro Cys Ile Asp Pro Ile Gly Tyr Thr Lys
        500                 505                 510

Gly Leu Ser Leu Gln Glu His Gln Ile Asn Val Lys Leu His Arg Asp
    515                 520                 525

Phe Ile Asn Glu Gln Met Asp Val Val Ser Leu Ser Lys Ala Arg Ile
530                 535                 540

Tyr Leu Asn Asp Arg Ile Lys Asn Glu Leu Ile Glu Val Arg Arg Asn
545                 550                 555                 560
```

```
Ile Arg Gln Arg Asn Val Lys Gly Val Asn Lys Ile Ala Lys Tyr Arg
            565                 570                 575

Asn Val Gly Ser His Ala Glu Thr Ser Ile Val His Glu Leu Asn His
        580                 585                 590

Pro Ala Thr Asn Glu Val Ile Ser Lys Met Glu Ser Ala Ser Gln Pro
        595                 600                 605

Glu His Cys Asp Asp Trp Asp Asn Phe Thr Ser Gly Leu Glu Pro Tyr
    610                 615                 620

<210> SEQ ID NO 5
<211> LENGTH: 335
<212> TYPE: PRT
<213> ORGANISM: Aeromonas salmonicida

<400> SEQUENCE: 5

Met Asp Leu Ser Cys His Asp Ala Asp Lys Leu Arg Ser Phe Ile Glu
1               5                   10                  15

Cys Tyr Val Glu Thr Pro Leu Leu Arg Ala Ile Gln Glu Asp Phe Asp
            20                  25                  30

Arg Leu Arg Phe Asn Lys Gln Phe Ala Gly Glu Pro Gln Cys Met Leu
        35                  40                  45

Leu Thr Gly Asp Thr Gly Thr Gly Lys Ser Ser Leu Ile Arg His Tyr
    50                  55                  60

Ala Ala Lys His Pro Glu Gln Val Arg His Gly Phe Ile His Lys Pro
65                  70                  75                  80

Leu Leu Val Ser Arg Ile Pro Ser Arg Pro Thr Leu Glu Ser Thr Met
                85                  90                  95

Val Glu Leu Leu Lys Asp Leu Gly Gln Phe Gly Ser Ser Asp Arg Ile
            100                 105                 110

His Lys Ser Ser Ala Glu Ser Leu Thr Glu Ala Leu Ile Lys Cys Leu
        115                 120                 125

Lys Arg Cys Glu Thr Glu Leu Ile Ile Ile Asp Glu Phe Gln Glu Leu
    130                 135                 140

Ile Glu Asn Lys Thr Arg Glu Lys Arg Asn Gln Ile Ala Asn Arg Leu
145                 150                 155                 160

Lys Tyr Ile Ser Glu Thr Ala Lys Ile Pro Ile Val Leu Val Gly Met
                165                 170                 175

Pro Trp Ala Thr Lys Ile Ala Glu Glu Pro Gln Trp Ser Ser Arg Leu
            180                 185                 190

Leu Ile Arg Arg Ser Ile Pro Tyr Phe Lys Leu Ser Asp Asp Arg Glu
        195                 200                 205

Asn Phe Ile Arg Leu Ile Met Gly Leu Ala Asn Arg Met Pro Phe Glu
    210                 215                 220

Thr Gln Ala Arg Leu Glu Thr Lys His Thr Ile Tyr Ala Leu Phe Ala
225                 230                 235                 240

Ala Cys Tyr Gly Ser Leu Arg Ala Leu Lys Gln Leu Leu Asp Glu Ser
                245                 250                 255

Val Lys Gln Ala Leu Ala Ala His Ala Glu Thr Leu Lys His Glu His
            260                 265                 270

Ile Ala Val Ala Tyr Ala Leu Phe Tyr Pro Asp Gln Val Asn Pro Phe
        275                 280                 285

Leu Gln Pro Ile Asp Glu Ile Lys Ala Cys Glu Val Lys Gln Tyr Ser
    290                 295                 300

Arg Tyr Glu Ile Asp Ala Ala Gly Lys Glu Glu Val Leu Asn Pro Leu
305                 310                 315                 320
```

Gln Phe Thr Asp Lys Ile Pro Ile Ser Gln Leu Leu Lys Lys Arg
            325                 330                 335

<210> SEQ ID NO 6
<211> LENGTH: 335
<212> TYPE: PRT
<213> ORGANISM: artificial sequence
<220> FEATURE:
<223> OTHER INFORMATION: modified TnsC protein

<400> SEQUENCE: 6

Met Asp Leu Ser Cys His Asp Ala Asp Lys Leu Arg Ser Phe Ile Glu
1               5                   10                  15

Cys Tyr Val Glu Thr Pro Leu Leu Arg Ala Ile Gln Glu Asp Phe Asp
            20                  25                  30

Arg Leu Arg Phe Asn Lys Gln Phe Ala Gly Pro Gln Cys Met Leu
        35                  40                  45

Leu Thr Gly Asp Thr Gly Thr Gly Lys Ser Ser Leu Ile Arg His Tyr
    50                  55                  60

Ala Ala Lys His Pro Glu Gln Val Arg His Gly Phe Ile His Lys Pro
65                  70                  75                  80

Leu Leu Val Ser Arg Ile Pro Ser Arg Pro Thr Leu Glu Ser Thr Met
                85                  90                  95

Val Glu Leu Leu Lys Asp Leu Gly Gln Phe Gly Ser Ser Asp Arg Ile
            100                 105                 110

His Lys Ser Ser Ala Glu Ser Leu Thr Glu Ala Leu Ile Lys Cys Leu
        115                 120                 125

Lys Arg Cys Glu Thr Glu Leu Ile Ile Ile Asp Ala Phe Gln Glu Leu
130                 135                 140

Ile Glu Asn Lys Thr Arg Glu Lys Arg Asn Gln Ile Ala Asn Arg Leu
145                 150                 155                 160

Lys Tyr Ile Ser Glu Thr Ala Lys Ile Pro Ile Val Leu Val Gly Met
                165                 170                 175

Pro Trp Ala Thr Lys Ile Ala Glu Glu Pro Gln Trp Ser Ser Arg Leu
            180                 185                 190

Leu Ile Arg Arg Ser Ile Pro Tyr Phe Lys Leu Ser Asp Asp Arg Glu
        195                 200                 205

Asn Phe Ile Arg Leu Ile Met Gly Leu Ala Asn Arg Met Pro Phe Glu
210                 215                 220

Thr Gln Ala Arg Leu Glu Thr Lys His Thr Ile Tyr Ala Leu Phe Ala
225                 230                 235                 240

Ala Cys Tyr Gly Ser Leu Arg Ala Leu Lys Gln Leu Leu Asp Glu Ser
                245                 250                 255

Val Lys Gln Ala Leu Ala Ala His Ala Glu Thr Leu Lys His Glu His
            260                 265                 270

Ile Ala Val Ala Tyr Ala Leu Phe Tyr Pro Asp Gln Val Asn Pro Phe
        275                 280                 285

Leu Gln Pro Ile Asp Glu Ile Lys Ala Cys Glu Val Lys Gln Tyr Ser
290                 295                 300

Arg Tyr Glu Ile Asp Ala Ala Gly Lys Glu Glu Val Leu Asn Pro Leu
305                 310                 315                 320

Gln Phe Thr Asp Lys Ile Pro Ile Ser Gln Leu Leu Lys Lys Arg
            325                 330                 335

<210> SEQ ID NO 7

<211> LENGTH: 335
<212> TYPE: PRT
<213> ORGANISM: artificial sequence
<220> FEATURE:
<223> OTHER INFORMATION: modified TnsC protein

<400> SEQUENCE: 7

```
Met Asp Leu Ser Cys His Asp Ala Asp Lys Leu Arg Ser Phe Ile Glu
1               5                   10                  15

Cys Tyr Val Glu Thr Pro Leu Leu Arg Ala Ile Gln Glu Asp Phe Asp
            20                  25                  30

Arg Leu Arg Phe Asn Lys Gln Phe Ala Gly Glu Pro Gln Cys Met Leu
        35                  40                  45

Leu Thr Gly Asp Thr Gly Thr Gly Lys Ser Ser Leu Ile Arg His Tyr
    50                  55                  60

Ala Ala Lys His Pro Glu Gln Val Arg His Gly Phe Ile His Lys Pro
65                  70                  75                  80

Leu Leu Val Ser Arg Ile Pro Ser Arg Pro Thr Leu Glu Ser Thr Met
                85                  90                  95

Val Glu Leu Leu Lys Asp Leu Gly Gln Phe Gly Ser Ser Asp Arg Ile
            100                 105                 110

His Lys Ser Ser Ala Glu Ser Leu Thr Glu Ala Leu Ile Lys Cys Leu
        115                 120                 125

Lys Arg Cys Glu Thr Glu Leu Ile Ile Ile Asp Gln Phe Gln Glu Leu
    130                 135                 140

Ile Glu Asn Lys Thr Arg Glu Lys Arg Asn Gln Ile Ala Asn Arg Leu
145                 150                 155                 160

Lys Tyr Ile Ser Glu Thr Ala Lys Ile Pro Ile Val Leu Val Gly Met
                165                 170                 175

Pro Trp Ala Thr Lys Ile Ala Glu Glu Pro Gln Trp Ser Ser Arg Leu
            180                 185                 190

Leu Ile Arg Arg Ser Ile Pro Tyr Phe Lys Leu Ser Asp Asp Arg Glu
        195                 200                 205

Asn Phe Ile Arg Leu Ile Met Gly Leu Ala Asn Arg Met Pro Phe Glu
    210                 215                 220

Thr Gln Ala Arg Leu Glu Thr Lys His Thr Ile Tyr Ala Leu Phe Ala
225                 230                 235                 240

Ala Cys Tyr Gly Ser Leu Arg Ala Leu Lys Gln Leu Leu Asp Glu Ser
                245                 250                 255

Val Lys Gln Ala Leu Ala Ala His Ala Glu Thr Leu Lys His Glu His
            260                 265                 270

Ile Ala Val Ala Tyr Ala Leu Phe Tyr Pro Asp Gln Val Asn Pro Phe
        275                 280                 285

Leu Gln Pro Ile Asp Glu Ile Lys Ala Cys Glu Val Lys Gln Tyr Ser
    290                 295                 300

Arg Tyr Glu Ile Asp Ala Ala Gly Lys Glu Val Leu Asn Pro Leu
305                 310                 315                 320

Gln Phe Thr Asp Lys Ile Pro Ile Ser Gln Leu Leu Lys Lys Arg
                325                 330                 335
```

<210> SEQ ID NO 8
<211> LENGTH: 109
<212> TYPE: PRT
<213> ORGANISM: Aeromonas salmonicida

<400> SEQUENCE: 8

```
Met Thr Asn Pro Leu Pro Ile Arg Leu Lys Ala Ala Arg Lys Ala Thr
1               5                   10                  15

Gly Leu Thr Gln Gln Leu Gly Ile Arg Leu Gly Met Glu Gln Ser
            20                  25                  30

Thr Ala Ser Ala Arg Met Asn Gln Tyr Glu Lys Gly Lys His Ala Pro
            35                  40                  45

Asp Tyr Gln Thr Met Gln Arg Ile Ala Gln Glu Leu Gly Tyr Pro Val
        50                  55                  60

Ala Tyr Phe Tyr Cys Asp Glu Leu Leu Ala Glu Leu Ile Cys Met
65              70                  75                  80

Met Ala Lys Leu Ser Glu Glu Lys Gln Arg Glu Leu Leu Gln Gln Leu
                85                  90                  95

Ser Val Thr Glu Tyr Ala Glu Ser Arg Asp Ser Ala Glu
            100                 105
```

<210> SEQ ID NO 9
<211> LENGTH: 68
<212> TYPE: DNA
<213> ORGANISM: Aeromonas salmonicida

<400> SEQUENCE: 9
tcaggaccgg aaggtagcag ccaaggcggg ggactcgagt gccgggatgt ggctgatggg    60
gccaccac                                                             68

<210> SEQ ID NO 10
<211> LENGTH: 32
<212> TYPE: RNA
<213> ORGANISM: artificial sequence
<220> FEATURE:
<223> OTHER INFORMATION: guide RNA

<400> SEQUENCE: 10
aggacuggaa gaaucaucc aaguugggga cu                                   32

<210> SEQ ID NO 11
<211> LENGTH: 32
<212> TYPE: DNA
<213> ORGANISM: artificial sequence
<220> FEATURE:
<223> OTHER INFORMATION: DNA equivalent of guide RNA

<400> SEQUENCE: 11
aggactggaa gaaatcatcc aagttgggga ct                                  32

<210> SEQ ID NO 12
<211> LENGTH: 32
<212> TYPE: RNA
<213> ORGANISM: artificial sequence
<220> FEATURE:
<223> OTHER INFORMATION: modified guide RNA

<400> SEQUENCE: 12
aggaccggaa gguagcagcc aaggcggggg ac                                  32

<210> SEQ ID NO 13
<211> LENGTH: 32
<212> TYPE: DNA
<213> ORGANISM: artificial sequence
<220> FEATURE:
<223> OTHER INFORMATION: artificial DNA sequence to match corrected gRNA
    sequence

<400> SEQUENCE: 13
aggaccggaa ggtagcagcc aaggcggggg ac                               32

<210> SEQ ID NO 14
<211> LENGTH: 4521
<212> TYPE: DNA
<213> ORGANISM: E. coli

<400> SEQUENCE: 14
cccaatacgc aaaccgcctc tccccgcgcg ttggccgatt cattaatgca gctggcacga    60
caggtttccc gactggaaag cgggcagtga gcgcaacgca attaatgtga gttagctcac   120
tcattaggca ccccaggctt tacactttat gcttccggct cgtatgttgt gtggaattgt   180
gagcggataa caatttcaca caggaaacag ctatgaccat gattacggat tcactggccg   240
tcgttttaca acgtcgtgac tgggaaaacc ctggcgttac ccaacttaat cgccttgcag   300
cacatccccc tttcgccagc tggcgtaata gcgaagaggc ccgcaccgat cgcccttccc   360
aacagttgcg cagcctgaat ggcgaatggc gctttgcctg gtttccggca ccagaagcgg   420
tgccggaaag ctggctggag tgcgatcttc ctgaggccga tactgtcgtc gtccccctcaa  480
actggcagat gcacggttac gatgcgccca tctacaccaa cgtgacctat cccattacgg   540
tcaatccgcc gtttgttccc acggagaatc cgacggtttg ttactcgctc acatttaatg   600
ttgatgaaag ctggctacag gaaggccaga cgcgaattat ttttgatggc gttaactcgg   660
cgtttcatct gtggtgcaac gggcgctggg tcggttacgg ccaggacagt cgtttgccgt   720
ctgaatttga cctgagcgca ttttttacgcg cggagaaaa ccgcctcgcg gtgatggtgc   780
tgcgctggag tgacggcagt tatctggaag atcaggatat gtggcggatg agcggcattt   840
tccgtgacgt ctcgttgctg cataaaccga ctacacaaat cagcgatttc catgttgcca   900
ctcgctttaa tgatgatttc agccgcgctg tactggaggc tgaagttcag atgtgcggcg   960
agttgcgtga ctacctacgg gtaacagttt ctttatggca gggtgaaacg caggtcgcca  1020
gcggcaccgc gccttcggc ggtgaaatta tcgatgagcg tggtggttat gccgatcgcg  1080
tcacactacg tctgaacgtc gaaaacccga aactgtggag cgccgaaatc ccgaatctct  1140
atcgtgcggt ggttgaactg cacaccgccg acggcacgct gattgaagca gaagcctgcg  1200
atgtcggttt ccgcgaggtg cggattgaaa atggtctgct gctgctgaac ggcaagccgt  1260
tgctgattcg aggcgttaac cgtcacgagc atcatcctct gcatggtcag gtcatggatg  1320
agcagacgat ggtgcaggat atcctgctga tgaagcagaa caactttaac gccgtgcgct  1380
gttcgcatta tccgaaccat ccgctgtggt acacgctgtg cgaccgctac ggcctgtatg  1440
tggtggatga agccaatatt gaaacccacg gcatggtgcc aatgaatcgt ctgaccgatg  1500
atccgcgctg gctaccggcg atgagcgaac gcgtaacgcg aatggtgcag cgcgatcgta  1560
atcacccgag tgtgatcatc tggtcgctgg ggaatgaatc aggccacggc gctaatcacg  1620
acgcgctgta tcgctggatc aaatctgtcg atccttcccg cccggtgcag tatgaaggcg  1680
gcggagccga caccacggcc accgatatta tttgcccgat gtacgcgcgc gtggatgaag  1740
accagccctt cccggctgtg ccgaaatggt ccatcaaaaa atggcttttcg ctacctggag  1800
agacgcgccc gctgatcctt tgcgaatacg cccacgcgat gggtaacagt cttggcggtt  1860
tcgctaaata ctggcaggcg tttcgtcagt atccccgttt acagggcggc ttcgtctggg  1920
actgggtgga tcagtcgctg attaaatatg atgaaacgg caaccgtgg tcggcttacg  1980
gcggtgattt tggcgatacg ccgaacgatc gccagttctg tatgaacggt ctggtctttg  2040

```
ccgaccgcac gccgcatcca gcgctgacgg aagcaaaaca ccagcagcag tttttccagt    2100
tccgtttatc cgggcaaacc atcgaagtga ccagcgaata cctgttccgt catagcgata    2160
acgagctcct gcactggatg gtggcgctgg atggtaagcc gctggcaagc ggtgaagtgc    2220
ctctggatgt cgctccacaa ggtaaacagt tgattgaact gcctgaacta ccgcagccgg    2280
agagcgccgg gcaactctgg ctcacagtac gcgtagtgca accgaacgcg accgcatggt    2340
cagaagccgg gcacatcagc gcctggcagc agtggcgtct ggcggaaaac ctcagtgtga    2400
cgctccccgc cgcgtcccac gccatcccgc atctgaccac cagcgaaatg gattttgca    2460 tcgagctggg taataagcgt tggcaattta accgccagtc aggctttctt tcacagatgt    2520
ggattggcga taaaaaacaa ctgctgacgc cgctgcgcga tcagttcacc cgtgcaccgc    2580
tggataacga cattggcgta agtgaagcga cccgcattga ccctaacgcc tgggtcgaac    2640
gctggaaggc ggcgggccat taccaggccg aagcagcgtt gttgcagtgc acggcagata    2700
cacttgctga tgcggtgctg attacgaccg ctcacgcgtg gcagcatcag gggaaaacct    2760
tatttatcag ccggaaaacc taccggattg atggtagtgg tcaaatggcg attaccgttg    2820
atgttgaagt ggcgagcgat acaccgcatc cggcgcggat tggcctgaac tgccagctgg    2880
cgcaggtagc agagcgggta aactggctcg gattagggcc gcaagaaaac tatcccgacc    2940
gccttactgc cgcctgtttt gaccgctggg atctgccatt gtcagacatg tatacccgt     3000 acgtcttccc gagcgaaaac ggtctgcgct gcggacgcg cgaattgaat tatggcccac    3060
accagtggcg cggcgacttc cagttcaaca tcagccgcta cagtcaacag caactgatgg    3120
aaaccagcca tcgccatctg ctgcacgcgg aagaaggcac atggctgaat atcgacggtt    3180
tccatatggg gattggtggc gacgactcct ggagcccgtc agtatcggcg gaattccagc    3240
tgagcgccgc tcgctaccat taccagttgg tctggtgtca aaataataa taaccgggca     3300 ggccatgtct cttgcgctcg ttcgccagcc aggacagaaa tgcctcgact tcgctgctgc    3360
ccaaggttgc cgggtgacgc acaccgtgga aacggatgaa ggcacgaacc cagtggacat    3420
aagcctgttc ggttcgtaag ctgtaatgca agtagcgtat gcgctcacgc aactggtcca    3480
gaaccttgac cgaacgcagc ggtggtaacg gcgcagtggc ggttttcatg gcttgttatg    3540
actgtttttt tggggtacag tctatgcctc gggcatccaa gcagcaagcg cgttacgccg    3600
tgggtcgatg tttgatgtta tggagcagca acgatgttac gcagcagggc agtcgcccta    3660
aaacaaagtt aaacatcatg agggaagcgg tgatcgccga agtatcgact caactatcag    3720
aggtagttgg cgtcatcgag cgccatctcg aaccgacgtt gctggccgta catttgtacg    3780
gctccgcagt ggatggcggc ctgaagccac acagtgatat tgatttgctg gttacggtga    3840
ccgtaaggct tgatgaaaca acgcggcgag ctttgatcaa cgaccttttg gaaacttcgg    3900
cttcccctgg agagagcgag attctccgcg ctgtagaagt caccattgtt gtgcacgacg    3960
acatcattcc gtggcgttat ccagctaagc gcgaactgca atttggagaa tggcagcgca    4020
atgacattct tgcaggtatc ttcgagccag ccacgatcga cattgatctg ctatcttgc    4080 tgacaaaagc aagagaacat agcgttgcct tggtaggtcc agcggcggag gaactctttg    4140
atccggttcc tgaacaggat ctatttgagg cgctaaatga aaccttaacg ctatggaact    4200
cgccgcccga ctgggctggc gatgagcgaa atgtagtgct tacgttgtcc cgcatttggt    4260
acagcgcagt aaccggcaaa atcgcgccga aggatgtcgc tgccgactgg gcaatggagc    4320
gcctgccggc ccagtatcag cccgtcatac ttgaagctag acaggcttat cttggacaag    4380
aagaagatcg cttggcctcg cgcgcagatc agttggaaga atttgtccac tacgtgaaag    4440
```

```
gcgagatcac caaggtagtc ggcaaataat gtctaacaat tcgttcaagc cgacgccgct    4500
tcgcggcgcg gcttaactca a                                              4521
```

<210> SEQ ID NO 15
<211> LENGTH: 32
<212> TYPE: RNA
<213> ORGANISM: artificial sequence
<220> FEATURE:
<223> OTHER INFORMATION: LacZ gRNA

<400> SEQUENCE: 15

```
uacggguaac aguuucuuua uggcagggug aa                                    32
```

<210> SEQ ID NO 16
<211> LENGTH: 32
<212> TYPE: DNA
<213> ORGANISM: artificial sequence
<220> FEATURE:
<223> OTHER INFORMATION: artificial spacer

<400> SEQUENCE: 16

```
tacgggtaac agtttcttta tggcagggtg aa                                    32
```

<210> SEQ ID NO 17
<211> LENGTH: 32
<212> TYPE: RNA
<213> ORGANISM: artificial sequence
<220> FEATURE:
<223> OTHER INFORMATION: LacZ4 guide RNA perfect match

<400> SEQUENCE: 17

```
acagcggaug guucggauaa ugcgaacagc gc                                    32
```

<210> SEQ ID NO 18
<211> LENGTH: 32
<212> TYPE: DNA
<213> ORGANISM: artificial sequence
<220> FEATURE:
<223> OTHER INFORMATION: artificial spacer

<400> SEQUENCE: 18

```
acagcggatg gttcggataa tgcgaacagc gc                                    32
```

<210> SEQ ID NO 19
<211> LENGTH: 130
<212> TYPE: DNA
<213> ORGANISM: E. coli

<400> SEQUENCE: 19

```
gcgagttgcg tgactaccta cgggtaacag tttctttatg gcagggtgaa acgcaggtcg      60
ccagcggcac cgcgcctttc ggcggtgaaa ttatcgatga tgtcgtctaa accataagtt     120
gacatatcta                                                            130
```

<210> SEQ ID NO 20
<211> LENGTH: 130
<212> TYPE: DNA
<213> ORGANISM: E. coli

<400> SEQUENCE: 20

```
ggtcgcacag cgtgtaccac agcggatggt tcggataatg cgaacagcgc acggcgttaa      60
agttgttctg cttcatcagc aggatatcct gcaccatcgt tgtcgtctaa accataagtt     120
```

```
gacatatcta                                                            130

<210> SEQ ID NO 21
<211> LENGTH: 128
<212> TYPE: DNA
<213> ORGANISM: artificial sequence
<220> FEATURE:
<223> OTHER INFORMATION: ffs sequence in E. coli

<400> SEQUENCE: 21
ttggccgcaa gaggattcag gaccggaagg tagcagccaa ggcgggggac tcgagtgccg     60
ggatgtggct gatgggcca ccaccttgcg ctcgttcgct gtcgtctaaa ccataagttg    120
acatatct                                                            128
```